(12) United States Patent
Feng et al.

(10) Patent No.: US 12,256,743 B2
(45) Date of Patent: Mar. 25, 2025

(54) SUGAR-PRODUCING AND TEXTURE-IMPROVING BAKERY METHODS AND PRODUCTS FORMED THEREFROM

(71) Applicant: Caravan Ingredients Inc., Lenexa, KS (US)

(72) Inventors: Guohua Feng, Overland Park, KS (US); Emily Guilfoyle, Overland Park, KS (US); Jesse Stinson, Overland Park, KS (US); Lawrence Skogerson, Mission Hills, KS (US)

(73) Assignee: Caravan Ingredients Inc., Lenexa, KS (US)

( * ) Notice: Subject to any disclaimer, the term of this patent is extended or adjusted under 35 U.S.C. 154(b) by 113 days.

(21) Appl. No.: 17/746,598

(22) Filed: May 17, 2022

(65) Prior Publication Data

US 2022/0279802 A1 Sep. 8, 2022

Related U.S. Application Data

(63) Continuation of application No. 14/793,992, filed on Jul. 8, 2015, now abandoned.

(60) Provisional application No. 62/021,899, filed on Jul. 8, 2014.

(30) Foreign Application Priority Data

Jul. 8, 2014 (EP) .................................. 14176074

(51) Int. Cl.
*A21D 13/062* (2017.01)
*A21D 8/04* (2006.01)
*C12N 9/26* (2006.01)
*C12N 9/28* (2006.01)

(52) U.S. Cl.
CPC ........... *A21D 13/062* (2013.01); *A21D 8/042* (2013.01); *A21D 8/047* (2013.01); *C12N 9/2411* (2013.01); *C12N 9/2417* (2013.01); *C12Y 302/01001* (2013.01); *C12Y 302/01* (2013.01); *C12Y 302/01003* (2013.01)

(58) Field of Classification Search
CPC ...... A21D 13/062; A21D 8/042; A21D 8/047; C12N 9/2411; C12N 9/2417; C12Y 302/01001; C12Y 302/01; C12Y 302/01003
USPC .......................................................... 426/20
See application file for complete search history.

(56) References Cited

U.S. PATENT DOCUMENTS

| | | | |
|---|---|---|---|
| 2,615,810 A * | 10/1952 | Stone | A21D 8/042 426/64 |
| 4,160,848 A | 7/1979 | Vidal et al. | |
| 4,247,637 A | 1/1981 | Tamura et al. | |
| 4,536,477 A | 8/1985 | Katkocin et al. | |
| 4,587,215 A * | 5/1986 | Hirsh | C12N 9/2428 435/911 |
| 4,598,048 A | 7/1986 | Diderichsen et al. | |
| 4,604,355 A | 8/1986 | Outtrup | |
| 5,023,094 A | 6/1991 | Van Eijk | |
| 5,059,430 A | 10/1991 | Bowles | |
| 5,589,207 A | 12/1996 | Larsen et al. | |
| 5,698,245 A | 12/1997 | Tanaka et al. | |
| 6,197,352 B1 | 3/2001 | Olesen | |
| 6,270,813 B1 | 8/2001 | Nielsen et al. | |
| RE38,507 E | 4/2004 | Olesen | |
| 6,896,916 B2 * | 5/2005 | Cooper | A21D 2/06 426/549 |
| 7,413,879 B2 | 8/2008 | Dunn-Coleman et al. | |
| 7,638,317 B2 | 12/2009 | Borch et al. | |
| 7,666,650 B2 | 2/2010 | Ye et al. | |
| 7,723,079 B2 | 5/2010 | Dunn-Coleman et al. | |
| 8,030,050 B2 | 10/2011 | Berg et al. | |
| 8,137,944 B2 | 3/2012 | Berg et al. | |
| 8,361,526 B2 | 1/2013 | Beier et al. | |
| 8,426,182 B1 | 4/2013 | Parenicova | |
| 8,551,755 B2 | 10/2013 | Aehle et al. | |
| 2001/0055635 A1 | 12/2001 | Spendler et al. | |
| 2003/0035876 A1 | 2/2003 | Kostival et al. | |
| 2006/0057250 A1 | 3/2006 | Jorgensen et al. | |

(Continued)

FOREIGN PATENT DOCUMENTS

| | | |
|---|---|---|
| CA | 2268966 | 5/1998 |
| EP | 0 135 138 | 3/1985 |

(Continued)

OTHER PUBLICATIONS

Christophersen et al., "Enzymatic Characterisation of Novamyl, a Thermostable alpha-Amylase," Starch—Staerke (Germany), vol. 50, Issue 1 (1998): 39-45 (abstract only attached).

(Continued)

*Primary Examiner* — Bhaskar Mukhopadhyay
(74) *Attorney, Agent, or Firm* — HOVEY WILLIAMS LLP

(57) ABSTRACT

Novel yeast-raised and other bakery products and methods of making those products are provided. The products are formed from dough comprising a thermally-stable amyloglucosidase, and a raw starch degrading amyloglucosidase and/or an anti-staling amylase. The level of added sugar included in the dough can be substantially reduced, and even eliminated, while still achieving a sweet product. Additionally, the resulting bakery product is free of, or at least substantially free of, fructose. The final baked product will also have improved texture properties, including superior firmness, resilience, and adhesiveness and can be made with a reduced amount of yeast.

16 Claims, 9 Drawing Sheets

(56) References Cited

U.S. PATENT DOCUMENTS

| | | | |
|---|---|---|---|
| 2006/0147581 | A1 | 7/2006 | Svendsen et al. |
| 2008/0293607 | A1 | 11/2008 | Jones et al. |
| 2009/0297659 | A1 | 12/2009 | Boutte et al. |
| 2010/0003366 | A1 | 1/2010 | Cuevas et al. |
| 2010/0062106 | A1 | 3/2010 | Mastenbroek et al. |
| 2010/0260517 | A1 | 10/2010 | Ishii |
| 2010/0273735 | A1 | 10/2010 | Deremaux et al. |
| 2011/0003031 | A1 | 1/2011 | Budolfsen et al. |
| 2011/0039308 | A1 | 2/2011 | Slupska et al. |
| 2011/0097778 | A1 | 4/2011 | Power et al. |
| 2011/0142994 | A1 | 6/2011 | Buwalda et al. |
| 2011/0165655 | A1 | 7/2011 | Svendsen et al. |
| 2011/0274786 | A1 | 11/2011 | Sorensen et al. |
| 2011/0300265 | A1 | 12/2011 | Feng et al. |
| 2011/0311678 | A1 | 12/2011 | Forman et al. |
| 2012/0151632 | A1 | 6/2012 | De Maria et al. |
| 2012/0156328 | A1 | 6/2012 | De Maria et al. |
| 2012/0164272 | A1 | 6/2012 | Van Benschop et al. |
| 2012/0251662 | A1 | 10/2012 | Stinson et al. |
| 2012/0288919 | A1 | 11/2012 | Mutsaers et al. |
| 2013/0059031 | A1 | 3/2013 | Else et al. |
| 2013/0209607 | A1* | 8/2013 | Rittig ............... A21D 8/042 426/18 |
| 2013/0216651 | A1 | 8/2013 | Bennedbaek-Jensen et al. |

FOREIGN PATENT DOCUMENTS

| | | |
|---|---|---|
| EP | 0 234 858 | 12/1993 |
| EP | 0412607 | 3/1994 |
| EP | 0 913 092 | 5/1999 |
| JP | 103-119949 | 5/1991 |
| JP | H04-207144 | 7/1992 |
| JP | H11-192052 | 7/1999 |
| WO | 86/01831 | 3/1986 |
| WO | 98/16112 | 4/1998 |
| WO | 99/28448 | 6/1999 |
| WO | 00/10395 | 3/2000 |
| WO | 00/27215 | 5/2000 |
| WO | 01/04273 | 1/2001 |
| WO | 2008/112727 | 9/2008 |
| WO | 2008/153815 | 12/2008 |
| WO | 2009/028448 | 3/2009 |
| WO | 2010/124975 | 11/2010 |
| WO | 2010/133644 | 11/2010 |
| WO | 2011/039324 | 4/2011 |
| WO | 2011/127802 | 10/2011 |
| WO | WO-2011127802 A1 * | 10/2011 ........... C12N 9/2428 |
| WO | 2012/010592 | 1/2012 |
| WO | 2012/088303 | 6/2012 |
| WO | 2013/028071 | 2/2013 |
| WO | 2017/205337 | 11/2017 |
| WO | 2021/160812 | 8/2021 |
| WO | 2022/061276 | 3/2022 |
| WO | 2022/090562 | 5/2022 |

OTHER PUBLICATIONS

Gerrard et al., "The Role of Maltodextrins in the Staling of Bread," Journal of Cereal Science, Academic Press Limited, vol. 26, No. 2, 1997, 201-209.

International Search Report and Written Opinion mailed Nov. 2, 2015, in corresponding PCT/EP2015/065612 filed Jul. 8, 2015.

Bergmann et al., "Selection of microorganisms which produce raw-starch degrading enzymes," Applied Microbiology and Biotechnology, Feb. 1988, vol. 27, Issue 5, pp. 443-446 (abstract only).

Dupont Danisco PowerFresh—Bakery Enzymes, www.danisco.com/product-range/food-enzymes/bakery-enzymes/powerfreshr/, 2 pages.

Fogarty et al., "Purification and Properties of a Thermophilic Amyloglucosidase from Aspergillus niger," Eur J Appl Microbiol Biotechnol (1983) 18: 271-278.

International Preliminary Report on Patentability issued Jan. 10, 2017 in corresponding PCT/EP2015/065612, 8 pages.

Office Action dated Jul. 14, 2017 in related U.S. Appl. No. 15/324,174, filed Jan. 5, 2017.

Office Action dated Dec. 15, 2017 in related U.S. Appl. No. 15/324,174, filed Jan. 5, 2017.

Office Action dated Mar. 26, 2018 in parent U.S. Appl. No. 14/793,992, filed Jul. 8, 2015, 19 pages.

Machine Translation in English of JP04-207144, 5 pages.

Office Action dated Dec. 14, 2018 in parent U.S. Appl. No. 14/793,992, filed Jul. 8, 2015, 20 pages.

May 20, 2019 Office Action in copending U.S. Appl. No. 15/966,860, 29 pages.

Jul. 25, 2019 Office Action in related U.S. Appl. No. 15/324,174, 15 pages.

Office Action dated Aug. 29, 19 in corresponding Chinese Patent Application No. 201580036530.4, English Language, 10 pages.

Office Action dated Aug. 29, 19 in corresponding Chinese Patent Application No. 201580036530.4, Chinese Language, 8 pages.

Office Action dated Jun. 26, 19 in parent U.S. Appl. No. 14/793,992, filed Jul. 8, 2015, 13 pages.

Copy of Office Action dated Jan. 10, 2020 in parent U.S. Appl. No. 14/793,992, filed Jul. 8, 2015, 24 pages.

"Amylase, " Wikipedia, 2019, 5 pages.

Office Action dated Nov. 22, 2019 in copending U.S. Appl. No. 15/966,860, filed Apr. 30, 2018, 18 pages.

Office Action dated Jan. 16, 2020 in related U.S. Appl. No. 15/324,174 filed Jan. 5, 2017, 26 pages.

Office Action dated May 27, 2020 in parent U.S. Appl. No. 14/793,992, filed Jul. 8, 2015, 13 pages.

EP Communication pursuant to Rule 114(2) EPC/Observations by a Third Party, dated Apr. 28, 2020 in corresponding EP15735944.9, 20 pages.

Bozic et al., "Raw starch degrading a-amylases: an unsolved riddle, " De Gruyter Open, Amylase 2017; 1: 12-25.

EP Communication pursuant to Rule 114(2) EPC/Observations by a Third Party, dated Mar. 13, 2019 in corresponding EP15735944.9, 32 pages.

Food Enzymes, Fermizyme AG 800, Gist-brocades Product Specifications, 2 pages.

Danisco Ingredients, "Baking trial regarding activity of AMG 300 L during baking," Karsten M. Kragh, Senior Scientist, Enzyme Development, Danisco Ingredients, Feb. 4, 1998, 3 pages.

Novo Enzymes, Produktblatt, AMG, Novo, Denmark, 2 pages.

Hyun et al., "General Biochemical Characterization of Thermostable Pullulanase and Glucoamylase from Clostridium thermohydrosulfuricum," Applied and Environmental Microbiology, May 1985, vol. 49, No. 5, p. 1168-1173.

Office Action dated Nov. 13, 2018 in copending U.S. Appl. No. 15/966,860, 14 pages.

Office Action dated Jun. 29, 2018 in related U.S. Appl. No. 15/324,174, 30 pages.

Office Action dated Nov. 29, 2018 in related U.S. Appl. No. 15/324,174, 14 pages.

Office Action dated Aug. 6, 2020 in copending U.S. Appl. No. 15/966,860, 26 pages.

Office Action dated May 12, 2020 in related U.S. Appl. No. 15/324,174, 20 pages.

Hebeda, Ronald E., Zobel, Henry F., eds., Baked Goods Freshness: Technology, Evaluation, and Inhibition of Staling, 1996, Marcel Dekker, Inc., New York, New York, pp. 114-116, 6 p. .

Kumar et al., "Microbial glucoamylases: characteristics and applications," Critical Reviews in Biotechnology, 2009, 29(3): 225-255, 31 pages.

Nielsen et al., "Cloning, heterologous expression, and enzymatic characterization of a thermostable glucoamylase from Talaromyces emersonii," Protein Expression and Purification 26 (2002) 1-8, 8 pages.

ExplorEnz—The Enzyme Database, EC 3.2.1.3, The Wayback Machine—https://web.archive.org/web/20131030103417/ . . . Archived Oct. 30, 2013, 1 page.

Declaration from Lene Kragh, European Patent Office in the Matter of Opposition to EP3166412B, Jan. 11, 2023, 5 pages.

Bakezyme Product Information, Lallemand, Apr. 1998, 2 pages.

(56) References Cited

OTHER PUBLICATIONS

Factsheet No. 23: Sugar and Bread, Federation of Bakers, Jan. 14, 2015, 2 pages.
McCance and Widdowson, The Composition of Foods, Sixth Edition, 2002, Cambridge: Royal Society of Chemistry, pp. 29-33, 8 pages.
European Patent Application No. 15735944.9/European Patent No. 3166412, Opposition filed, Jan. 19, 2023, 75 pages.
Notification of Reasons for Refusal dated Feb. 7, 2018 in corresponding Japanese Patent Application No. JP2016-576024, 8 pages.
Decision of Refusal dated Nov. 12, 2018 in corresponding Japanese Patent Application No. JP2016-576024, 6 pages.
Decision to Grant dated May 27, 2019 in corresponding Japanese Patent Application No. JP2016-576024, 4 pages.
Office Action dated Nov. 8, 2017 in corresponding Canadian Patent Application No. 2,954,220, 3 pages.
Office Action dated Dec. 4, 2018 in corresponding Canadian Patent Application No. 2,954,220, 3 pages.
Office Action dated Aug. 13, 2019 in corresponding Canadian Patent Application No. 2,954,220, 3 pages.
Notice of Preliminary Examination Office Action dated Nov. 7, 2019 in corresponding Brazilian Patent Application No. BR112017000004-0, 4 pages.
Decision to Grant dated Oct. 26, 2021 in corresponding Brazilian Patent Application No. BR112017000004-0, 4 pages.
Machine Translation of Notice of Preliminary Examination Office Action dated Nov. 7, 2019 in corresponding Brazilian Patent Application No. BR112017000004-0, 4 pages.
Machine Translation of Notification of Reasons for Refusal dated Feb. 7, 2018 in corresponding Japanese Patent Application No. JP2016-576024, 8 pages.
Machine Translation of Decision of Refusal dated Nov. 12, 2018 in corresponding Japanese Patent Application No. JP2016-576024, 6 pages.
Machine Translation of Decision to Grant dated May 27, 2019 in corresponding Japanese Patent Application No. JP2016-576024, 4 pages.
Machine Translation of Decision to Grant dated Oct. 26, 2021 in corresponding Brazilian Patent Application No. BR112017000004-0, 4 pages.
Starch / 2001-11693-02.pdf Product Sheet, AMG 300 L, Novozymes, 1 page.

* cited by examiner

SUGAR-PRODUCING AND TEXTURE-IMPROVING BAKERY METHODS AND PRODUCTS FORMED THEREFROM

RELATED APPLICATION

This application is a continuation application of U.S. patent application Ser. No. 14/793,992, which is pending and entitled SUGAR-PRODUCING AND TEXTURE-IMPROVING BAKERY METHODS AND PRODUCTS FORMED THEREFROM, filed Jul. 8, 2015, incorporated by reference herein. U.S. patent application Ser. No. 14/793,992 claims the priority benefit of U.S. Provisional Patent Application No. 62/021,899, entitled BAKERY PRODUCTS FORMED USING NO ADDED SUGAR AND METHODS OF MAKING THE SAME, filed Jul. 8, 2014, incorporated by reference herein. U.S. patent application Ser. No. 14/793,992 also claims priority to European Patent Application No. 14176074.4, filed on Jul. 8, 2014, incorporated by reference herein.

BACKGROUND OF THE INVENTION

Field of the Invention

The present invention is broadly concerned with the preparation of bakery products by incorporating a specific enzyme formulation that generates sugar during baking. Advantageously, the final product is free of, or substantially free of, added sugar and fructose, while still having a taste and flavor equal to or better than equivalent products made with added sugar. Additionally, the present invention significantly improves the textural quality and shelf-life of the bakery products through the synergistic interactions of the included enzymes.

Description of the Prior Art

Bakery products are generally appealing to consumers due to their freshness and sweet taste. With prior art products, this is due to the addition of sugars, such as sucrose, high fructose corn syrup, honey, etc., to the ingredients used to form the products. Recently, added sugar has been singled out as one of the unhealthiest ingredients in food. Added sugars contain high levels of fructose (generally 50%), which has been associated with potential health risks. Fructose is metabolized in the liver, resulting in harmful end products like triglycerides, uric acid, and free radicals. This can lead to health ailments such as non-alcoholic fatty liver disease, increased LDL cholesterol, cardiovascular disease, gout, and/or higher triglycerides, among other things.

Thus, it would be preferable to avoid adding added sugars, especially fructose-containing added sugars, to these products. However, the sweet taste is desirable for the products to be appealing, so simply not adding sugar would lead to products having a poor taste and lacking consumer appeal. The use of artificial sweetening products in place of sugar leads to problems of its own, including potential health issues, a taste that is not appealing to some people, and the consumer-unfriendly ingredient labeling. Also, while sugar alcohols have become a popular way to sweeten products, they also do not have as appealing of a taste as typical sugars, and many people cannot digest sugar alcohols properly.

There is a need for a process for forming these products that does not require the inclusion of the added sugars. Furthermore, it would be highly desirable if the final products were free of, or substantially free of, fructose while still having an appealing and sweet taste.

SUMMARY OF THE INVENTION

The present invention is broadly concerned with a method of forming a bakery product, where the method comprises providing a dough comprising:
  yeast;
  an initial quantity of sugar;
  a source of starch;
  a thermally-stable amyloglucosidase that exhibits activity at temperatures at which the starch gelatinizes; and
  an enzyme selected from the group consisting of:
    raw starch degrading amyloglucosidases;
    anti-staling amylases; and
    mixtures thereof.
The dough is baked for a time and temperature sufficient to yield the bakery product, with the bakery product having a final quantity of sugar that is greater than the initial quantity of sugar.

The invention also provides a dough useful for forming a yeast-raised bakery product and comprising a source of starch, yeast, and water. The improvement is that the dough comprises a thermally-stable amyloglucosidase that exhibits activity at temperatures at which the starch gelatinizes, and an enzyme selected from the group consisting of:
  raw starch degrading amyloglucosidases;
  anti-staling amylases; and
  mixtures thereof; and.

In a further embodiment, the invention provides a yeast-raised bakery product formed from flour, yeast, and water. The improvement is that the product comprises:
  an inactivated, thermally-stable amyloglucosidase derived from a thermally-stable amyloglucosidase that exhibits activity at temperatures at which starch gelatinizes;
  at least about 5% by weight sugar, based upon the total weight of the bakery product taken as 100% by weight; and
  less than about 0.5% by weight fructose, based upon the total weight of the bakery product taken as 100% by weight.
A further improvement is that the bakery product comprises a decrease in crumb firmness by at least about 50%, preferably at least about 75%, and more preferably from about 90% to about 100%, when compared to the same product formed from ingredients where about 8% added sugar is included in the initial ingredients and either without the enzyme formulations of the present invention or with a current market standard anti-staling enzymatic product, such as the Ultra Fresh Premium 250 from Corbion illustrated in FIGS. 7 and 11.

The bakery product furthermore comprises an improvement of crumb resilience by at least about 10%, preferably at least about 15%, and more preferably from about 20% to about 28%, when compared to the same product formed from ingredients where about 8% added sugar is included in the initial ingredients and with a conventional enzyme, such as AMG 1100 from Novozymes, or a current market standard anti-staling enzymatic product, such as the Ultra Fresh Premium 250 from Corbion illustrated in FIGS. 2 and 12.

Yet a further improvement of the bakery product is a decrease of crumb adhesiveness by at least about 10%, preferably at least about 25%, and more preferably from about 25% to about 50%, when compared to the same product formed from ingredients where a conventional enzyme, such as AMG 1100 from Novozymes, was included, as illustrated in FIG. 3.

DETAILED DESCRIPTION OF THE PREFERRED EMBODIMENTS

Figure 1:
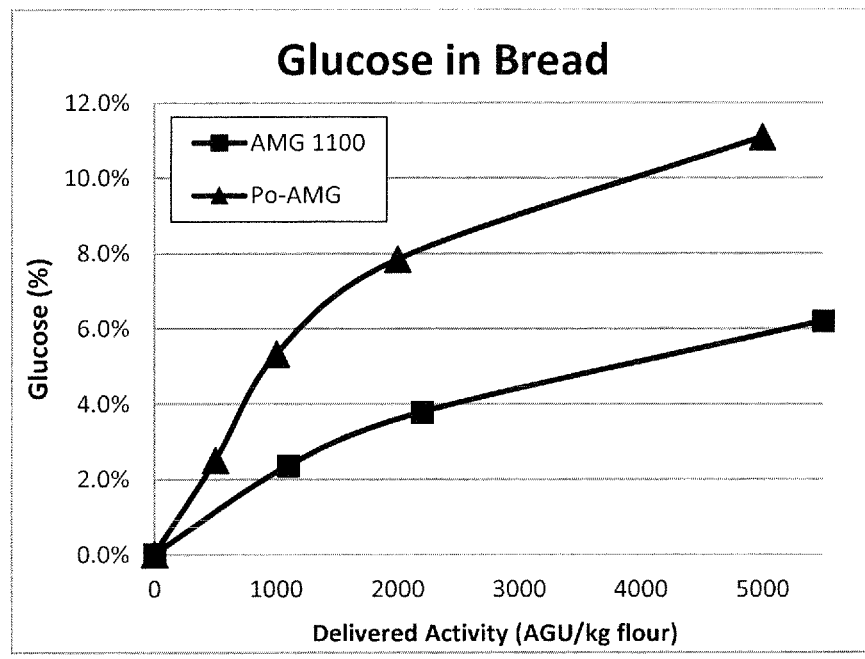
FIG. 1 is a graph comparing the sugar production capabilities of a conventional RSD amyloglucosidase (AMG 1100) to a thermally-stable amyloglucosidase (Po-AMG) from Example 1.

In more detail, the present invention is concerned with novel dough formulations as well as novel methods of making yeast-raised, bakery products, and other bakery products with these formulations. These products include those selected from the group consisting of breads, pretzels, English muffins, buns, rolls, tortillas (both corn and flour), pizza dough, bagels, and crumpets.

In the inventive methods, ingredients for the particular product are mixed together. Typical ingredients and their preferred ranges are set forth in Table 1.

TABLE 1

| INGREDIENT | BROAD RANGE* | PREFERRED* | MOST PREFERRED* |
| --- | --- | --- | --- |
| Yeast Compressed | from about 1% to about 10% | from about 2% to about 6% | from about 3% to about 4% |
| Dough Strengthener | from about 0% to about 2% | from about 0.25% to about 1% | from about 0.35% to about 0.5% |
| Added Sugar** | less than about 10% | less than about 3% | about 1% |
| Dry Milk | from about 0% to about 3% | from about 1% to about 2% | from about 1% to about 1.5% |
| Salt (typically NaCl) | from about 1% to about 3% | from about 1.5% to about 2.5% | from about 1.75% to about 2.25% |
| Mold Inhibitor | from about 0% to about 1% | from about 0.1% to about 0.5% | from about 0.25% to about 0.35% |
| Oil/Fat | from about 0% to about 20% | from about 1% to about 6% | from about 2% to about 3% |
| Flour Improver | from about 0 ppm to about 500 ppm | from about 10 ppm to about 200 ppm | from about 40 ppm to about 75 ppm |
| Emulsifiers | from about 0% to about 4% | from about 0.5% to about 3% | from about 1% to about 2.5% |
| Water | from about 50% to about 75% | from about 55% to about 70% | from about 58% to about 65% |
| Thermally-Stable Amyloglucosidase | at least about 300 AGU/kg flour | from about 500 to about 1,500 AGU/kg flour | from about 750 to about 1,250 AGU/kg flour |

TABLE 1-continued

| INGREDIENT | BROAD RANGE* | PREFERRED* | MOST PREFERRED* |
| --- | --- | --- | --- |
| Raw Starch Degrading Amyloglucosidase | from about 0 to about 5,000 AGU/kg flour | from about 100 to about 2,500 AGU/kg flour | from about 500 to about 1,000 AGU/kg flour |
| Bacterial Amylase | from about 0 to 20,000 MANU/kg flour | from about 1,000 to about 10,000 MANU/kg flour | from about 3,000 to about 5,000 MANU/kg flour |
| Other Enzymes | from about 0 ppm to about 2,000 ppm | from about 20 ppm to about 300 ppm | from about 100 ppm to about 200 ppm |

*Percentage or ppm based upon the weight of flour.
**Refers to all types of added sugar present in the formulation. Sugars that can be added to the formulation include sucrose, glucose, fructose, high fructose corn syrup, honey, brown sugar, lactose, galactose, maple syrup, and rice syrup. "Added sugar" does not include sugar that could be inherently present in other ingredients (e.g., as part of the flour) in the dough mixture, nor does it include sugar alcohols (e.g., xylitol, sorbitol) or artificial sweetening ingredients.

In a particularly preferred embodiment, the added sugar is about 0% by weight, and in another embodiment the added sugar is 0% by weight.

MANUs and AGUs are measures of the enzymatic activity of an amylase and an amyloglucosidase, respectively. As used herein, one unit of MANU (Maltogenic Amylase Novo Unit) is defined as the amount of enzyme required to release one μmol of maltose per minute at a concentration of 10 mg of maltotriose (Sigma M 8378) substrate per ml of 0.1 M citrate buffer, pH 5.0 at 37° C. for 30 minutes. One unit of AGU (Amyloglucosidase Unit) is defined as the amount of enzyme required to hydrolyze 1 μmol maltose per minute at a substrate concentration of 100 milimole maltose in a 0.1 M acetate buffer, pH 4.3 at 37° C. In either instance, the amounts of maltose in μmols can be determined by comparing the final solution to a standard maltose solution.

In addition to the ingredients from Table 1, the dough will include a source of starch, such as those selected from the group consisting of wheat flour, rye flour, oat flour, barley flour, triticale flour, rice flour, tapioca starch, corn starch, wheat starch, rice starch, potato starch, corn flour, and potato flour. The source of starch will typically be included to provide levels of from about 50% to about 95% by weight starch, and preferably from about 65% to about 85% by weight starch, based upon the total weight of the flour taken as 100% by weight. When flour is the source of starch, this will typically result in flour levels of from about 40% to about 70% by weight flour, and preferably from about 50% to about 60% by weight flour, based upon the total weight of the dough taken as 100% by weight.

The yeast used can be any yeast conventionally used in yeast-raised bakery products, with cream and compressed yeast being preferred. Suitable dough strengtheners include those selected from the group consisting of sodium stearoyl lactylate, ethoxylated monoglyceride, diacetyl tartaric acid esters of mono- and diglycerides (DATEM), and mixtures thereof.

Preferred mold inhibitors include those selected from the group consisting of calcium and/or sodium propionate, potassium sorbate, vinegar, raisin juice concentrate, and mixtures thereof. The preferred oil or fat is selected from the group consisting of soy oil, partially hydrogenated soy oil, lard, palm oil, corn oil, cottonseed oil, canola oil, and mixtures thereof.

Suitable flour improvers include those selected from the group consisting of ascorbic acid, potassium bromate, potassium iodate, azodicarboamide, calcium peroxide, and mixtures thereof. While any conventional emulsifier can be utilized, preferred emulsifiers include polyoxyethylene sorbitan monostearate (typically referred to as Polysorbate 60) and monoglycerides, such as powdered and hydrated monoglycerides, citrated monoglycerides, and succinylated monoglycerides.

Thermally-Stable Amyloglucosidases

The dough will also include a thermally-stable amyloglucosidases. The thermally-stable amyloglucosidase utilized in the present invention should be selected so that it is active and available to act on starch as it gelatinizes during the baking process. That is, the bulk of the starch present in the dough prior to baking is in the form of a starch granule, which is not readily acted upon by enzymes. The raw starch will begin to gelatinize at about 65° C. and is typically fully gelatinized by around 85° C. Gelatinized starch is more easily hydrolyzed into glucose by amyloglucosidases. Thus, the selected thermally-stable amyloglucosidase should be sufficiently heat-stable that it is able to act on the starch in the dough as the dough transitions to bread (i.e., it should be active, or at least partially active, from about 65° C. to about 85° C.). At the same time, it is preferred that the selected thermally-stable amyloglucosidase is inactivated by the end of baking (i.e., about 95° C. to about 100° C.) as residual amyloglucosidase activity in fully baked products can negatively affect the quality of the final product during its shelf life.

Thus, thermally-stable amyloglucosidases for use in the present invention will have a half-life ($T_{1/2}$) of from about 1 minute to about 30 minutes at about 85° C., preferably from about 3 minutes to about 20 minutes at about 85° C., and more preferably from about 5 minutes to about 15 minutes at about 85° C. These values are obtained at a pH of 4.5 and in 0.12 mM $CaCl_2$.

In one embodiment, the preferred thermally-stable amyloglucosidase will have an optimum temperature of at least about 60° C., preferably from about 60° C. to about 85° C., more preferably from about 70° C. to about 85° C., and even more preferably from about 75° C. to about 80° C., when assayed at a pH of about 4.5. As used herein, "optimum temperature" of an enzyme refers to the temperature at which the enzyme activity is highest at the designated assay condition.

In one embodiment, the thermally-stable amyloglucosidases utilized will have a residual enzyme activity of from about 25% to about 90%, preferably from about 35% to about 70%, and more preferably from about 35% to about 60% after about 15 minutes incubation at 85° C. In order to avoid a negative impact on the cooked bread, the selected thermally-stable amyloglucosidases will have a residual enzyme activity of less than about 15%, preferably less than about 10%, and more preferably less than about 5% after about 3 minutes at 100° C. in a 5.0 pH buffer with 0.12 mM CaCl$_2$. As used herein, "residual enzyme activity" is the enzymatic activity (in MANUs or AGUs, as defined above) remaining after the particular enzyme has been subjected to the conditions set forth in this paragraph (i.e., "final activity"). The "% residual enzyme activity" is calculated by comparing the enzymatic activity (in MANUs or AGUs, as defined above) remaining after the particular enzyme has been subjected to the conditions set forth in this paragraph (i.e., "final enzymatic activity), to the enzymatic activity (again, in MANUs or AGUs) of the same enzyme prior to being subjected to these conditions (i.e., "initial enzymatic activity). Thus, $$\% \text{ Residual Activity} = \left(\frac{\text{Final Enzymatic Activity}}{\text{Initial Enzymatic Activity}}\right) \times 100.$$

In one embodiment, the thermally-stable amyloglucosidases utilized will have an optimal pH (i.e., the pH at which the enzyme activity is highest at the designated assay condition) of from about 3.0 to about 7.0, preferably from about 4.0 to about 6.0, and more preferably from about 4.5 to about 5.5 when assayed with 1 mM CaCl$_2$.

In one embodiment, the preferred thermally-stable amyloglucosidase will have a pH stability range of from about 3.0 to about 7.0, preferably from about 4.0 to about 6.0, and more preferably from about 4.5 to about 5.5. pH stability is measured by first incubating the particular enzyme at the designated pH for 20 hours at 37° C. The retained enzyme activity is then assayed and compared to the original enzyme activity. The preferred thermally-stable amyloglucosidase will retain at least about 70%, preferably at least about 90%, and more preferably from about 95% to 100% of its original activity in the pH stability ranges mentioned above.

Specific examples of thermally-stable amyloglucosidases suitable for use in the present invention include amyloglucosidases derived from strains (i.e., encoded by a DNA sequence found in one of the strains) selected from the group consisting of:
  (a) *Penicillium oxalicum* (such as Po-AMG that described in International Publication No. 2011/127802 by Novozymes, incorporated by reference herein);
  (b) *Talaromyces emersonii* (such as that described in International Publication No. 2009/028448, incorporated by reference herein);
  (c) *Talaromyces duponti* (such as that described in U.S. Pat. No. 4,247,637, incorporated by reference herein); *Talaromyces thermophilius* (such as that described in U.S. Pat. No. 4,587,215, incorporated by reference herein);
  (e) *Clostridium thermoamylolyticum* (such as that described in EP 135,138, incorporated by reference herein); and
  (f) *Clostridium thermohydrosulfuricum* (such as that described in International Publication No. 1986/001,831, incorporated by reference herein).

Although the above sets forth some preferred thermally-stable amyloglucosidases, any thermally-stable amyloglucosidase meeting the above described properties can work with the present invention. This includes amyloglucosidases from any natural source, as well as variants made through gene modification.

Raw Starch Degrading Amyloglucosidases

In a preferred embodiment, a raw starch degrading amyloglucosidase is present in the dough. A raw starch degrading amyloglucosidase acts on raw starch molecules. In one embodiment, this raw starch degrading amyloglucosidase preferably has a lower optimal temperature than the first amyloglucosidase described above. Also, this raw starch degrading amyloglucosidase only needs to be moderately thermally stable. That is, it may lose most of its activity when the dough temperature is above the starch gelatinization temperature. In a preferred embodiment, sugar is generated by the raw starch degrading amyloglucosidase only in the dough, but not during baking. That is, raw starch degrading enzymes (such as those sold under the names AMG 300 and AMG 1100) lose most of their activity at temperature at which starch gelatinizes.

Preferred raw starch degrading amyloglucosidases will have heat stability up to about 70° C., but will preferably lose activity rather rapidly above 70° C. Thus, preferred raw starch degrading amyloglucosidases for use in the present invention will have a half-life ($T_{1/2}$) of from about 1 minute to about 20 minutes at about 70° C., preferably from about 3 minutes to about 15 minutes at about 70° C., and more preferably from about 3 minutes to about 10 minutes at about 70° C. Preferably, the raw starch degrading amyloglucosidases utilized will have a residual activity of at least about 5%, preferably at least about 10%, and more preferably from about 10% to about 20% after about 15 minutes at 70° C. In another embodiment, the raw starch degrading amyloglucosidase will have an optimum temperature of less than about 70° C., preferably less than about 65° C., more preferably from about 40° C. to about 65° C., more preferably from about 40° C. to about 60° C., and even more preferably from about 45° C. to about 55° C., at a pH of about 4.5.

Suitable raw starch degrading amyloglucosidases are disclosed in International Publication No. 2012/088303 and *Purification and Properties of a Thermophilic Amyloglucosidase* from *Aspergillus niger*, W. Fogarty et. al., Eur J Appl Microbiol Biotechnol (1983) 18:271-278, incorporated by reference herein. Those produced from *Aspergillus* are preferred, and particularly preferred include those derived from strains selected from the group consisting of *Aspergillus niger* (such as that sold under the name AMG® 1100, by Novozymes, Denmark).

Anti-Staling Amylases

In another embodiment, a bacterial or anti-staling amylase is included. It is preferred that the amylase be one that is inactivated between about 80° C. and about 90° C., because starch hydrolyzation by the anti-staling amylase occurs much more effectively when starch granules get gelatinized during baking. The most preferred anti-staling amylase is a maltogenic amylase, more preferably a maltogenic α-amylase, and even more preferably a maltogenic α-exoamylase. The most preferred such amylase is sold under the name NOVAMYL by Novozymes A/S and is described in U.S. Pat. No. RE38,507, incorporated by reference herein. This maltogenic amylase is producible by *Bacillus* strain NCIB 11837, or one encoded by a DNA sequence derived from *Bacillus* strain NCIB 11837 (the maltogenic amylase is disclosed in U.S. Pat. Nos. 4,598,048 and 4,604,355, the contents of which are incorporated herein by reference). Another maltogenic amylase which may be used in the present process is a maltogenic β-amylase, producible by *Bacillus* strain NCIB 11608 (disclosed in EP 234 858, the contents of which are hereby incorporated by reference). Another suitable anti-staling enzyme for use in the present invention is available from DuPont Danisco under the names POWERFresh® G4 and POWERFresh® G+. Additionally, U.S. Patent Application Publication No. 2009/0297659 (incorporated by reference herein) discloses suitable amylases.

Some of the other enzymes that can be included in the invention in addition to the maltogenic amylase include those selected from the group consisting of fungal amylases, bacterial alpha-amylase from *Bacillus subtilis*, hemi-cellulases, xylanases, proteases, glucose oxidase, hexose oxidase, lipase, phospholipase, asparaginase, and cellulases.

As noted above, in some embodiments, the invention utilizes only a thermally-stable amyloglucosidase. In a preferred embodiment, the invention utilizes a raw starch degrading amyloglucosidase or an anti-staling amylase in addition to the thermally-stable amyloglucosidase. In a particularly preferred embodiment, the invention utilizes a thermally-stable amyloglucosidase, a raw starch degrading amyloglucosidase, and an anti-staling amylase. Of course, the embodiment can be selected depending upon the user's preferences and the particular product to be prepared.

Method of Making Baked Products

In forming the dough according to the invention, the above ingredients can be simply mixed together in one stage using the "no-time dough process," or they can be subjected to the "sponge and dough process." In the "no-time dough process," all ingredients are added to a mixing bowl at the same time and mixed for a time period from about 5 to about 15 minutes to form the mixed dough.

In the "sponge and dough" process, part of the flour (e.g., 55-75% by weight of the total flour) is mixed with water, yeast, and preferably the dough strengthener (if utilized) and allowed to ferment for a time period of from about 3 hours to about 4 hours. This forms the "sponge." After this time period, the remaining ingredients are mixed with the sponge for a time period of from about 2 minutes to about 10 minutes to form the mixed dough. The mixed dough is preferably allowed to rest for a time period of from about 5 minutes to about 15 minutes before being formed into the desired size pieces and placed in the baking pans. The dough is then preferably allowed to proof at a temperature of from about 40° C. to about 50° C. at a relative humidity of from about 65% to about 95% for a time period of from about 50 minutes to about 70 minutes.

During proofing, the enzymes present will begin to act on the starch. Any raw starch degrading amyloglucosidase present will begin to act on the raw starch, as will the thermally-stable amyloglucosidase, converting some starch into glucose.

Regardless of the embodiment, sugars (and particularly non-fructose sugars) are generated during the baking (and preferably also during proofing) process by the enzyme blend utilized. That is, the starting ingredients or dough will contain some "initial quantity" of sugar. That initial quantity could be zero, such as in no added sugar formulations. Or, that initial quantity could be some low-sugar amount (e.g., 1-3%) or an amount as high as 10%, as described above. More specifically, the initial quantity of sugar is about 10% by weight or less, preferably less than about 3% by weight, more preferably less than about 1% by weight. In a particularly preferred embodiment, the initial quantity of sugar is about 0% by weight. Regardless of the initial quantity, after baking the final product will have a final quantity of total sugar that is greater than the initial quantity. For the purpose of the invention, sugar or sugars are understood to include sucrose, glucose, fructose, high fructose corn syrup, honey, brown sugar, lactose, galactose, maple syrup, and rice syrup, but not sugar alcohols or artificial sweetening ingredients.

In more detail, in some embodiments the initial dough of the invention (i.e., prior to proofing) contains little to no sugar (beyond minor amounts of sugars found in any flour or starch by nature or being inherently present due to the type of any flour or starch used), and particularly little to no fructose (i.e., less than about 0.2% by weight, preferably less than about 0.1%, and preferably about 0% by weight of each, based upon the total weight of the initial dough taken as 100% by weight). In one embodiment, the initial dough will also contain little to no glucose (in the same low quantities as set forth above for fructose in the initial dough). During proofing, both raw starch degrading amyloglucosidase and thermally-stable amyloglucosidase will convert certain amount of starch to glucose. After the dough is proofed, there will typically be total sugar levels (i.e., total glucose, fructose, and maltose) of at least about 1% by weight, preferably from about 1% to about 2% by weight, and more preferably from about 2% to about 3% by weight, based upon the total weight of the proofed dough taken as 100% by weight. The glucose levels in the proofed dough will typically be at least about 1% by weight, preferably from about 1% to about 2% by weight, and more preferably from about 2% to about 3% by weight, based upon the total weight of the proofed dough taken as 100% by weight. Thus, the glucose present in the dough after proofing will generally increase from 0% (or close to 0%) to at least about 1%, preferably to about 1% to about 2%, and more preferably from about 2% to about 3% by weight, based upon the total weight of the proofed dough taken as 100% by weight. When there is at least some amount of glucose present in the initial ingredient mixture (i.e., the glucose present in the initial ingredients is greater than 0%, while still being within the limits set forth above), the total glucose present in the proofed dough will be at least about 5 times, preferably at least about 10 times, and more preferably from about 10 to about 15 times that of the glucose quantity present in the dough prior to proofing. Advantageously, the fructose levels noted above will remain substantially unchanged. That is, the proofed dough will still have less than about 0.2% by weight fructose, preferably less than about 0.1% by weight fructose, and more preferably about 0% by weight fructose, based upon the total weight of the proofed dough taken as 100% by weight.

After proofing, the product can then be baked using the times and temperatures necessary for the type of product being made (e.g., from about 190° C. to about 220° C. for about 20 minutes to about 30 minutes). While any non-thermally-stable enzymes, including any raw starch degrading amyloglucosidases that were included in the original ingredients will still be present in their active forms during proofing, they will begin to be inactivated during baking, leaving behind the enzyme skeletons. However, the thermally-stable amyloglucosidase(s) and the anti-staling amylase included in the initial ingredients will still be present in its active form as baking is commenced. Thus, as the starch granules gelatinize during baking, the thermally-stable amyloglucosidase will be able to continue to hydrolyze the gelatinized starch, further producing glucose in higher quantities, whereas the anti-staling amylase will also continue to hydrolyze the gelatinized starch, leaving an anti-staling effect in the finished product, and also producing maltose, other oligosaccharides, and dextrins. However, by the end of the bake cycle, both the thermally-stable amyloglucosidase and the anti-staling amylase will be inactivated.

The invention results in a number of advantages, in addition to those discussed previously. The present invention results in the use of significantly less yeast than in prior art products. Thus, using the previously mentioned enzyme formulations of the present invention yields a yeast reduction of at least about 15%, preferably at least about 20%, and more preferably from about 20% to about 35%, when compared to the same product formed from ingredients where sugar is added to the initial ingredients and without the enzyme formulations of the present invention. For example, when a dough with 0% added sugar in the initial ingredients is utilized in combination with the enzyme formulations of the present invention, the above yeast reductions are achieved when compared to the same product formed from ingredients where 8% added sugar is included in the initial ingredients and without the enzyme formulations of the present invention.

Figure 7:
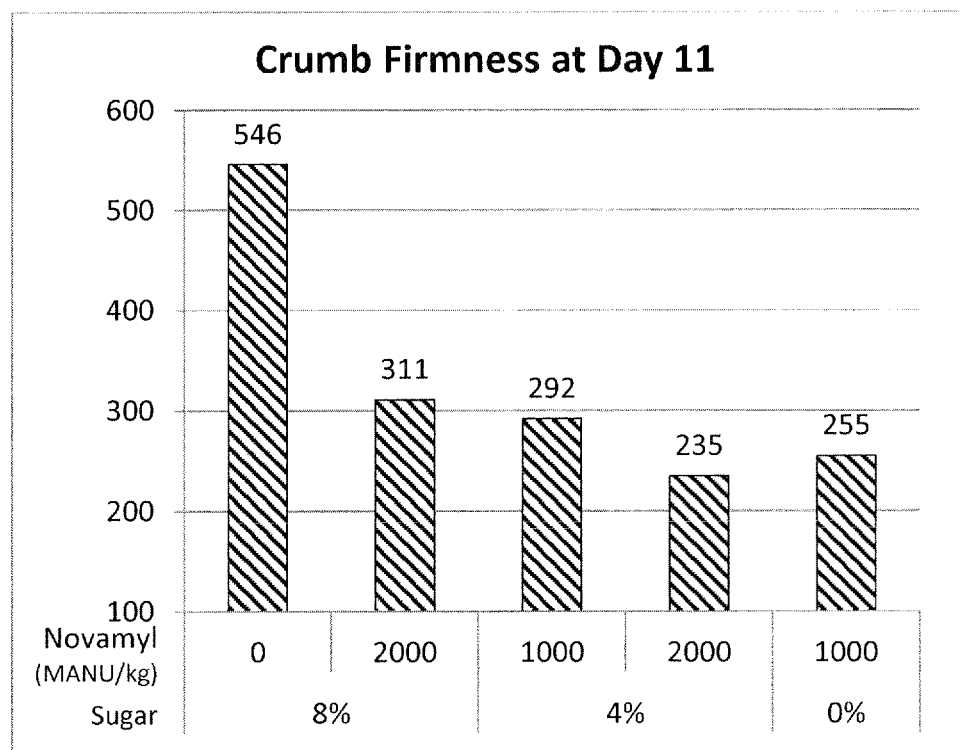
FIG. 7 is a graph showing the effects of reducing the added sugar, or sucrose, in dough formulas on the performance of anti-staling enzymes in terms of reducing the crumb firmness from Example 3.
Figure 11:
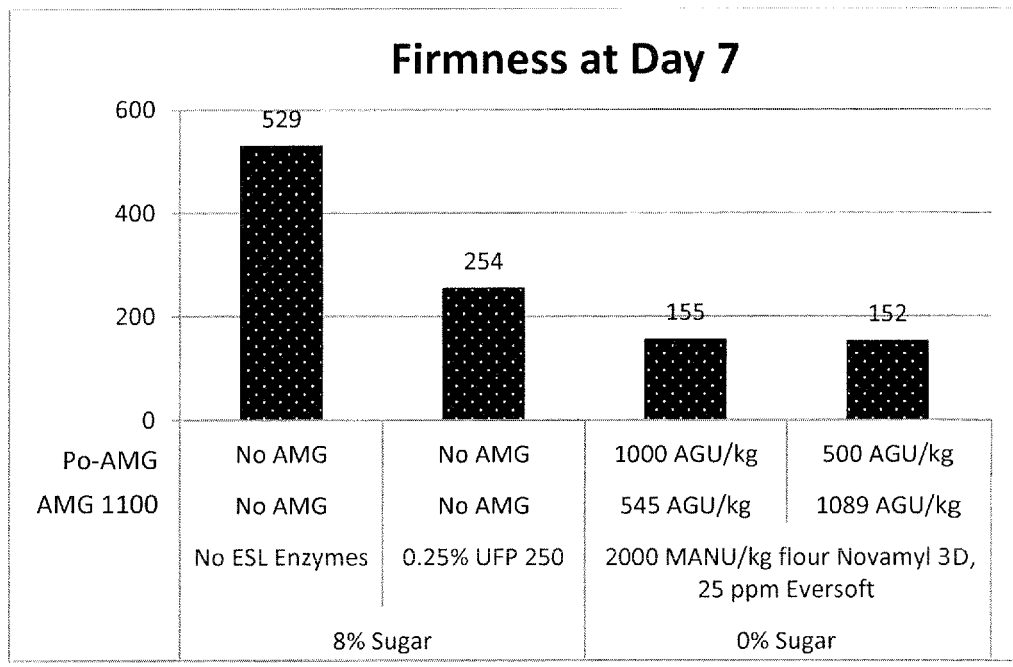
FIG. 11 is a graph of the firmness of the different bread formulations in Example 4.

An additional advantage of the present invention is the increased functionality of the anti-staling maltogenic amylase (measured as crumb firmness). That is, the use of a thermally-stable amyloglucosidase allows for lower quantities of sugar, such as sucrose, to be added to the starting dough, which in turn improves the performance of anti-staling amylases, since most of the added sugars inhibit the anti-staling maltogenic amylase. It was observed that a dough with the enzyme formulations of the present invention and 0% added sugar in the initial ingredients yields a decrease in crumb firmness by at least about 50%, preferably at least about 75%, and more preferably from about 90% to about 100%, when compared to the same product formed from ingredients where 8% added sugar is included in the initial ingredients and without the enzyme formulations of the present invention, or with a current market standard anti-staling enzymatic product, such as the Ultra Fresh Premium 250 from Corbion, which are illustrated in FIGS. 7 and 11.

Additionally, even though little to no added sugars (and, therefore, little to no fructose) were included when forming the initial dough, the final baked product formed utilizing the enzyme formulations of the present invention is as sweet or sweeter, when compared to an 8% sugar (or sucrose) control product in a sensory test. That is, the baked product will typically have total sugar levels (mainly the non-fructose-containing glucose and maltose) of at least about 5% by weight, preferably from about 6% to about 12% by weight, and more preferably from about 8% to about 10% by weight, based upon the total weight of the final, baked, bakery product taken as 100% by weight. When there is at least some sugar present in the initial ingredients (i.e., the amount of sugar in the initial ingredients is greater than 0%), the total sugars present in the final baked product will generally be at least about 5 times, preferably at least about 10 times, and more preferably from about 16 to about 20 times that of the total sugars present in the initial ingredient mixture.

The glucose levels in the final baked product will typically be at least about 3% by weight, preferably from about 3% to about 10% by weight, and more preferably from about 4% to about 6% by weight, based upon the total weight of the bakery product taken as 100% by weight. Thus, when there is at least some amount of glucose present in the initial ingredients, the glucose present in the dough in the final baked product will generally be at least about 15 times, preferably at least about 20 times, and more preferably from about 20 to about 30 times that of the glucose quantity present in the initial ingredient formulation.

Again, and advantageously, the fructose levels noted above will remain substantially unchanged. That is, the final baked product will have less than about 1% by weight fructose, preferably less than about 0.5% by weight fructose, and more preferably less than about 0% by weight fructose, based upon the total weight of the bakery product taken as 100% by weight. It will be appreciated that this presents a significant advantage over the prior art because the health risks associated with fructose consumption are avoided.

As discussed above, in one embodiment the invention involves the use of a thermally-stable amyloglucosidase together with an anti-staling (maltogenic) amylase. Since both thermally-stable amyloglucosidases and anti-staling amylases have similar thermal stabilities and both remain active after starch granules gelatinize, they work synergistically during baking. Advantageously, the presence of the thermally-stable amyloglucosidases not only increases the sweet taste of the baked products, but also decreases the crumb adhesiveness and increases the crumb resilience. The invention further allows for the level of expensive anti-staling amylases to be reduced, while improving the texture and still achieving a sweet bread. Thus, bakery products formed according to the present invention not only have improved crumb texture due to reduced firmness, reduced adhesiveness, and increased crumb resilience, but these products also have improved taste and flavor due to the small sugars, such as glucose and maltose, produced by the thermally-stable amyloglucosidases and the anti-staling amylases.

Regardless of the embodiment, when subjected to the firmness (i.e., crumb compressibility) test described in the TEST METHODS section below, bakery products according to the invention will give results of less than about 250 g of force at day 7, preferably less than about 200 g of force, and even more preferably less than about 160 g of force. Furthermore, when subjected to the adhesiveness test described in that same section, bakery products according to the invention will give a value of from about 5 g*mm to about 25 g*mm, preferably from about 5 g*mm to about 20 g*mm, and more preferably from about 10 g*mm to about 20 g*mm when measured at shelf life day 7. The percent resilience achieved will be at least about 28%, preferably from about 30% to about 40%, and more preferably from about 32% to about 37% when measured shelf life day 7. Finally, when the final baked product is bread, the specific volume is at least about 5.5 g/cc$^3$, preferably at least about 6.0 g/cc$^3$, and more preferably at least about 6.5 g/cc$^3$, in a 454 g piece of bread. The volume is determined by VolScan laser volumeter manufactured by Stable Micro Systems.

EXAMPLES

The following examples set forth preferred methods in accordance with the invention. It is to be understood, however, that these examples are provided by way of illustration and nothing therein should be taken as a limitation upon the overall scope of the invention.

Test Methods

Texture Analysis

The bread texture was measured at day 7 and day 14. After baking, the bread was cooled to an internal temperature of 100° F. (50 minutes), then weighed, measured for volume, and stored in a temperature-controlled room at 72° F.+/−2° F. until testing. At that time, the loaves were sliced one loaf at a time with an Oliver 16 blade slicer to a thickness of 25 mm+/−2 mm to produce 10 slices per one pound loaf. The center four slices were tested using Texture Profile Analysis (TPA) procedure. The measuring instrument was a Texture Analyzer from Stable Micro Systems (TA-XT2 Texture Analyzer—25 kg load cell with 1 g resolution). The software running this instrument was Texture Expert Exceed version 2.64. The settings for running the TPA on the Texture Analyzer for bread are in the table below.

Texture Analyzer Settings

| Test Mode and Option | TPA |
|---|---|
| Pre-Test Speed (mm/sec) | 2.00 |
| Test Speed (mm/sec) | 1.00 |
| Post Test Speed (mm/sec) | 1.00 |
| Target Mode | Strain |
| Strain | 25% |
| $2^{nd}$ Strain | 40% |
| Time (sec) | 3 |
| Holding Time on $2^{nd}$ Compression (sec) | 3 |
| Trigger Type | Auto |
| Trigger Force (grams) | 5 |
| Units Force | Grams |
| Units Distance | Millimeters |

It will be appreciated that one skilled in the art would be able to adjust these settings based upon the type of product being tested. For example, the Distance (depth of test in mm) could be adjusted depending upon the type of product tested.

A TA-4 probe (1½ inch-38 mm diameter acrylic cylinder) was used, and graph preferences were set to Time and auto range on the X axis, and Force and auto range on the Y axis.

The procedure for measuring the bread was to lay a single slice on the platform of the Texture Analyzer, position it so the probe was approximately in the center of the slice and about 10 mm above the surface, and start the test program. The test generated a graph that was used to quantify adhesiveness, firmness, and resilience. Specifically, the adhesiveness, or adhesive value, is the negative area following the end of the second curve and representing the energy needed to withdraw the probe from the slice. The firmness is the force point on the first curve corresponding to a punch depth of 25% of the slice thickness. Resilience is the ratio of the energy released from the slice when the probe is lifted from the slice to the energy applied to the slice when the probe is compressing the slice (AACC Method 74-09).

Sugar Extraction and Analysis

The sugar content of both the dough and bread was tested by measuring a 20 g sample of dough or bread crumb in a blending cup. Next, 80 g of distilled water was added, and the hand-held blender was used to disperse the dough or crumb completely. About 12 ml of the mixture was poured into a 15 ml tube and placed on ice. The tube was then centrifuged at 4,000 rpm for 10 minutes. The supernatant was then removed (making sure to obtain the clear solution in the middle of the tube) and then transferred into two microfuge tubes. For dough extraction, the supernatant was boiled in the microfuge tube for 1 minute, and then cooled on ice. The microfuge tubes were centrifuged at 12,000 rpm for 10 minutes. The resulting supernatant was then transferred to two new labeled microfuge tubes, which were stored in the refrigerator until sugar analysis.

Sugar content in the samples was analyzed on Dionex Ultimate 3000 RS HPLC system with Dionex CarboPac PA1 column (4×250 mm) with a PA10 guard column (4×50 mm). The electrochemical detector used was Dionex ED40 with Thermo Scientific's disposable electrodes. The HPLC mobile phase A was 50 mM NaOH, while the mobile phase B was 200 mM NaOH. All sugar samples were filtered through 0.4 µm filter before loading to the HPLC column.

Example 1

Amyloglucosidase Sugar Production and Texture Modification

A conventional raw starch degrading ("RSD") amyloglucosidase, AMG 1100 (from Novozymes®, North Carolina), was compared to a thermally-stable amyloglucosidase, Po-AMG (from Novozymes®), in bread baking for their sugar production and crumb texture modification capabilities. A standard white pan bread formulation was prepared according to the following process.

White Straight Pan Bread

| Ingredients | % of flour weight | Gram |
|---|---|---|
| Flour | 100.0 | 700.00 |
| DEPENDOX ® AXC[A] | 0.04 | 0.28 |
| Salt | 2.0 | 14.00 |
| Granulated sugar (sucrose) | 1.0 | 7.00 |
| Calcium Propionate | 0.3 | 2.10 |
| Soy Oil | 2.0 | 14.00 |
| Yeast-compressed | 7.00 | 49.00 |
| Water | 64.0 | 448.00 |
| GMS 90 SS[B] | 1.0 | 7.00 |
| Sodium Stearoyl Lactylate (SSL) | 0.35 | 2.45 |
| UFP 250[C] | 0.50 | 3.50 |
| Total Weight | | 176.3 |

[A] A blend of ascorbic acid, azodi carbonamide (ADA), fungal enzymes, and wheat starch (available from Corbion, Lenexa, KS).
[B] Hydrated monoglycerides (emulsifier; available from Corbion).
[C] Ultra Fresh Premium 250 (shelf-life extending enzymes; available from Corbion).

Amyloglucosidase

| Name | AGU/g | Optimal Temp | Opt. pH | Half Time |
|---|---|---|---|---|
| AMG 1100 | 1100/g | 65-70° C. | 4-5 | 7 min @ 70° C. |
| Po-AMG | 1680/g | 75-80° C. | 4-5 | 120 min @ 70° C.; 10 min @ 85° C. |

The amounts of amyloglucosidase were varied accordingly, as shown in the Table below.

Formula Variations

| | Dough # | | | | | | | |
|---|---|---|---|---|---|---|---|---|
| | 1 | 2 | 3 | 4 | 5 | 6 | 7 | 8 |
| | | AMG 1100 | | | | Po-AMG | | |
| AGU/kg flour | 0 | 1,000 | 2,000 | 5,000 | 500 | 1,000 | 2,000 | 5,000 |

The ingredients were added to a Hobart mixer, and mixed on low for 1 minute and then on high for 13 minutes. The mixer bowl was chilled by circulating 20° C. chilling water through the cooling jackets of the mixing bowl. After mixing, the dough was allowed to rest on a wood bench for 10 minutes and then, divided, sheeted, and moulded according to the processing parameters in the table below.

Processing Parameters

| | |
|---|---|
| Targeted Dough Temperature | 78° F. (circulating 20° C. chilling water) |
| Floor Time | 10 min |
| Divided Dough Wt. | 525 g |
| Rest after Rounding | 5 min |
| Mould Type and Settings | |
| Mould Type | Straight grain |
| 2nd Roller | 2 |
| Pressure Bd. | 2.8 |
| Proofer Setting | 104° F., 95% RH |
| Proof Time | Time to a targeted height |
| Baking Temp | 420° F. |
| Baking Time | 20 min |
| Cooling Time at Room Temperature | 60 min |

The moulded dough pieces were then placed into loaf pans and proofed to the targeted height for around 55-60 min. Before baking, a sample of each proofed dough was taken for sugar extraction and analysis. After baking, the loaves were left on a metal shelf for cooling for 60 minutes and then packed individually in plastic bags for shelf life analysis, which included textural analysis with a Texture analyzer and sugar content analysis as described above.

Figure 2:
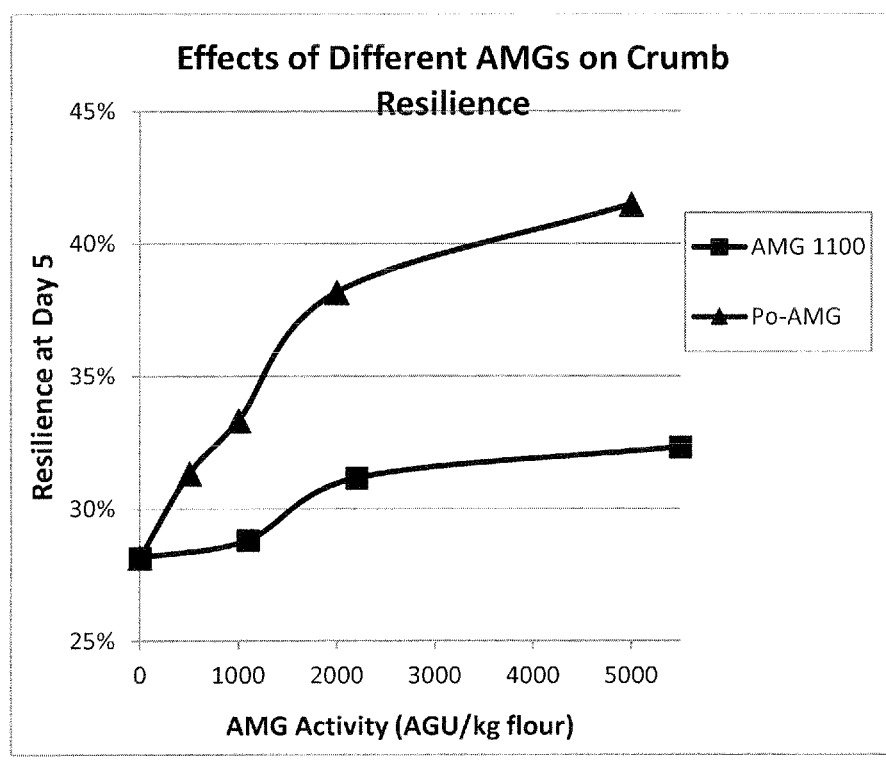
FIG. 2 is a graph comparing the bread resilience modification capabilities of a conventional RSD amyloglucosidase (AMG 1100) to a thermally-stable amyloglucosidase (Po-AMG) from Example 1.
Figure 3:
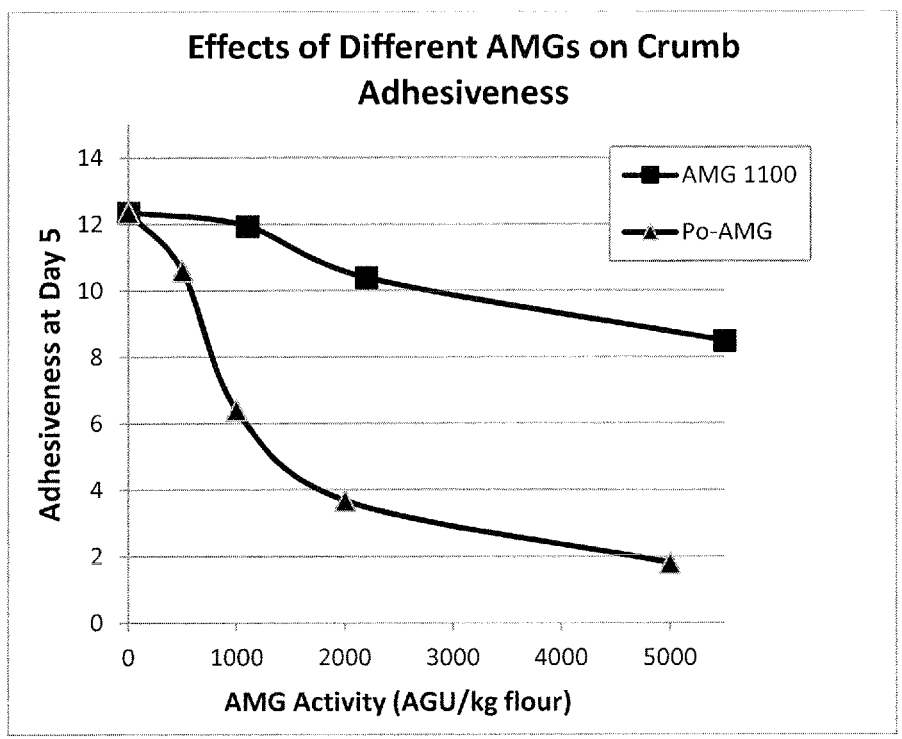
FIG. 3 is a graph comparing the bread adhesiveness modification capabilities of a conventional RSD amyloglucosidase (AMG 1100) to a thermally-stable amyloglucosidase (Po-AMG) from Example 1.

FIG. 1 compares the sugar production capabilities of a conventional RSD amyloglucosidase, AMG 1100, to a thermally-stable amyloglucosidase, Po-AMG. The results showed that the thermally-stable amyloglucosidase, Po-AMG, is more effective in producing glucose in the bread, mainly due to its ability to continue converting starch into glucose after the raw starch was gelatinized at temperatures above 65° C. FIGS. 2 and 3 compare the bread texture modification capabilities of a conventional RSD amyloglucosidase, AMG 1100, to a thermally-stable amyloglucosidase, Po-AMG. The results clearly show that the thermally-stable amyloglucosidase, Po-AMG, had much greater texture modification capability, in terms of increasing crumb resilience and reducing crumb adhesiveness.

Based on the data illustrated in FIG. 2, an improvement of crumb resilience by at least about 10%, preferably at least about 15%, and more preferably from about 20% to about 28%, can be achieved by including various levels of Po-AMG in the dough, compared to the same product formed from ingredients where a conventional enzyme, such as AMG 1100 from Novozymes, was included in the dough. Meanwhile as illustrated in FIG. 3, a decrease of crumb adhesiveness by at least about 10%, preferably at least about 25%, and more preferably from about 25% to about 79%, can be achieved by including various levels of Po-AMG in the dough, compared to the same product formed from ingredients where a conventional enzyme, such as AMG 1100 from Novozymes, was included in the dough.

Example 2

Analysis of Sugar Production Capability

A standard white pan bread formulation was prepared according to the following formulation and the same processing parameters described in Example 1. All of the bread dough was made with 1% added-sugar and specified amounts of amyloglucosidases.

White Straight Pan Bread

| Ingredients | % of flour weight | Gram |
|---|---|---|
| Flour | 100.0 | 700.00 |
| DEPENDOX ® AXC | 0.04 | 0.28 |
| Salt | 2.0 | 14.00 |
| Granulated sugar (sucrose) | 1.0 | 7.00 |
| Calcium Propionate | 0.3 | 2.10 |
| Soy Oil | 2.0 | 14.00 |
| Yeast-compressed | 5.50 | 38.50 |
| Water | 64.0 | 448.00 |
| GMS 90 SS | 1.0 | 7.00 |
| SSL | 0.35 | 2.45 |
| NOVAMYLS ® 3D[4] | 0.02 | 0.14 |
| Total Weight | | 174.8 |

[4]An anti-staling enzyme from Novozymes ®.

Formula Variations

| | AGU/kg flour | | | |
|---|---|---|---|---|
| Dough # | 1 | 2 | 3 | 4 |
| AMG 1100 | 0 | 0 | 1000 | 1000 |
| Po-AMG | 0 | 1000 | 0 | 1000 |

Figure 4:
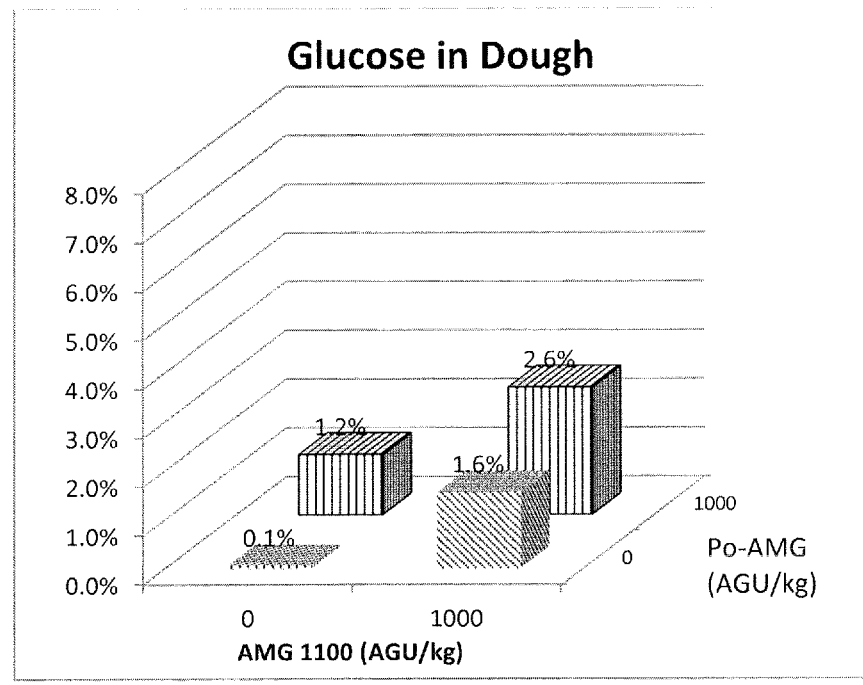
FIG. 4 is a graph illustrating that both a conventional RSD amyloglucosidase (AMG 1100) and a thermally-stable amyloglucosidase (Po-AMG) can be used to produce small amounts of sugar during the dough mixing and dough proofing stages from Example 2.
Figure 5:
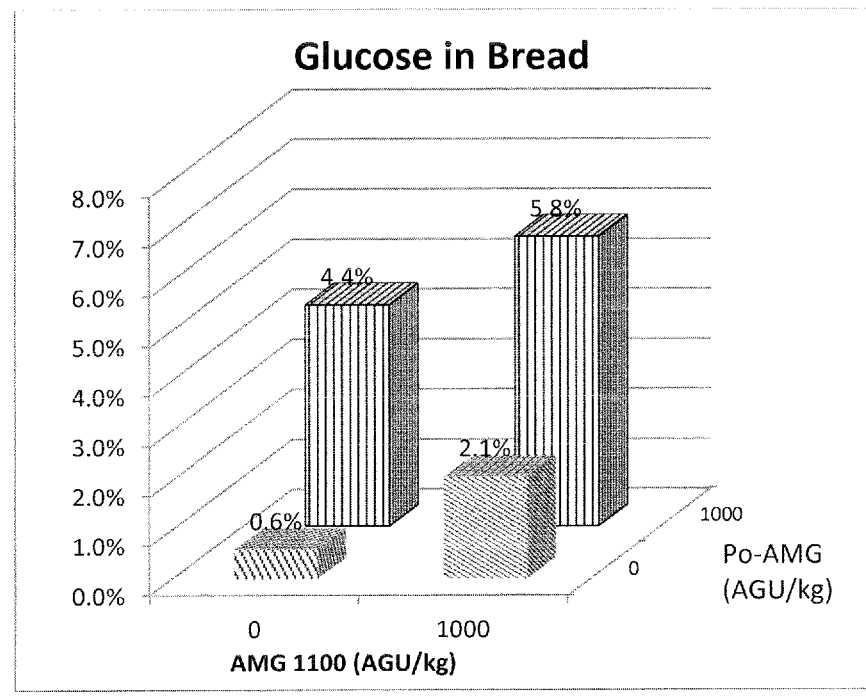
FIG. 5 is a graph illustrating the total amounts of glucose produced by either a RSD amyloglucosidase (AMG 1100), or a thermally-stable amyloglucosidase (Po-AMG), or the combination of the two in finished bread from Example 2.
Figure 6:
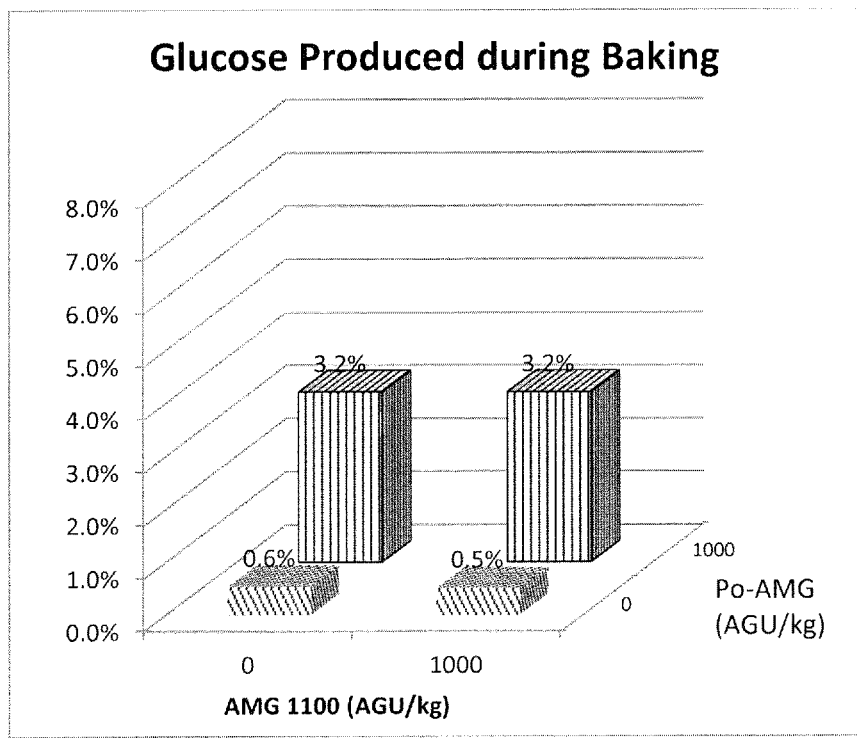
FIG. 6 is a graph illustrating that a significant amount of glucose can only be produced by a thermally-stable amyloglucosidase (Po-AMG), whereas the conventional amyloglucosidase (AMG 1100) was not able to produce a significant amount of glucose during baking from Example 2.

Again, samples of proofed dough were collected and flash frozen for sugar analysis. Dough sugar was extracted as described above, except that 10 g of dough was dispersed in 90 g of water. The results are shown in FIGS. 4-6. Sugar content in the proofed dough and in the baked bread was analyzed and compared to determine when the sugars were produced during the process of bread making.

Sugar Analysis

| | 0 AGU/kg flour Po-AMG | 1000 AGU/kg flour Po-AMG |
|---|---|---|
| Glucose in proofed dough | | |
| 0 AGU/kg flour AMG 1100 | 0.06% | 1.23% |
| 1000 AGU/kg flour AMG 1100 | 1.56% | 2.60% |
| Glucose in Bread | | |
| 0 AGU/kg flour AMG 1100 | 0.61% | 4.44% |
| 1000 AGU/kg flour AMG 1100 | 2.08% | 5.81% |
| Maltose in Dough | | |
| 0 AGU/kg flour AMG 1100 | 1.92% | 0.61% |
| 1000 AGU/kg flour AMG 1100 | 0.00% | 0.00% |
| Maltose in Bread | | |
| 0 AGU/kg flour AMG 1100 | 7.29% | 5.60% |
| 1000 AGU/kg flour AMG 1100 | 7.24% | 5.76% |
| Glucose Produced during Baking | | |
| 0 AGU/kg flour AMG 1100 | 0.55% | 3.21% |
| 1000 AGU/kg flour AMG 1100 | 0.52% | 3.21% |

FIGS. 4 to 6 show that the amyloglucosidases were used to produce glucose in different stages during the bread making process. FIG. 4 shows that a RSD amyloglucosidase, such as AMG 1100, can be used to produce sugar during dough mixing and dough proofing stages; whereas a more thermally-stable amyloglucosidase, such as Po-AMG, is much more effective in producing sugar during the actual baking stage (see FIGS. 5 and 6). FIG. 6 showed that only the thermally-stable amyloglucosidase, such as Po-AMG used in this invention, produced a significant amount of glucose during baking, whereas the conventional amyloglucosidase, such as AMG 1100 from *Aspergillus niger*, was not able to produce significant amounts of glucose during baking since it was inactivated before the starch granules were gelatinized. However, by using a combination of two different types of amyloglucosidases, sugar, and most significantly glucose, can be produced throughout the entire bread making process, which can maximize the sugar (particularly glucose) content in the finished baked products, provide sufficient glucose for yeast fermentation during dough proofing, and give a desirable sweet taste of the finished baked products. Furthermore, as shown in the table above, significant amounts of maltose were produced, entirely during baking by the thermally stable anti-staling maltogenic amylase. The high amount of maltose in the baked product also contributed to the flavor and taste of the baked products.

Example 3

Sugar Content and its Effect on Anti-Staling Enzyme

A standard white pan bread formulation was prepared according to the following formulation. Five different formulations were prepared by varying the amount of sugar added to the formulation, the level of anti-staling enzyme (NOVAMYL®), and the amount of amyloglucosidase, Po-AMG, and other ingredients were varied accordingly, as shown in the Tables below.

White Straight Pan Bread

| Ingredients | % of flour weight | Gram |
|---|---|---|
| Flour | 100.0 | 700 |
| DEPENDOX ® AXC | 0.06 | 0.42 |
| Salt | 2.0 | 14 |
| Granulated sugar (sucrose) | Vary | Vary |
| Calcium Propionate | 0.2 | 1.4 |
| SSL (optional) | 0.35 | 2.45 |
| GMS-90 (optional) | 1.00 | 7 |
| Soy Oil | 2.0 | 14 |
| 1% BXP 25001 | 0.10 | 0.7 |
| Yeast-dry | Vary | Vary |
| Water | Vary | Vary |
| Total Weight | Vary | Vary |

Formula Variations

| Dough # | 1 | 2 | 3 | 4 | 5 |
|---|---|---|---|---|---|
| Po-AMG | 0 AGU/kg flour | | 1000 AGU/kg flour | | |
| Sugar (sucrose-% of flour weight) | 8% | | 4% | | 0% |
| Novamyl (MANU/kg flour) | 0 | 2000 | 1000 | 2000 | 1000 |
| Yeast-dry (% of flour weight) | 3.0 | 3.0 | 2.5 | 2.5 | 2.0 |
| Water (% of flour weight) | 62.0 | 62.0 | 63.0 | 63.0 | 64.0 |

By using the inventive enzyme compositions, added-sugars can be significantly reduced or completely removed from bread formulas, which greatly enhance the functionality of anti-staling enzymes, such as NOVAMYL®.

FIG. 7 shows that by reducing the amount of added sugar in the dough formula, the anti-staling function of NOVAMYL® is greatly enhanced. In this bake test, we showed that 1000 MANU/kg flour of NOVAMYL® at 4% added-sugar and 1000 AGU/kg flour of Po-AMG had similar crumb softening effect as 2000 MANU/kg flour of NOVAMYL® with 8% added-sugar and 0 AGU/kg flour of Po-AMG; whereas 1000 MANU/kg flour of NOVAMYL® with 0% added-sugar and 1000 AGU/kg flour of Po-AMG performed significantly better than 2000 MANU/kg flour of NOVAMYL® with 8% added-sugar and 0 AGU/kg flour of Po-AMG.

Figure 8:
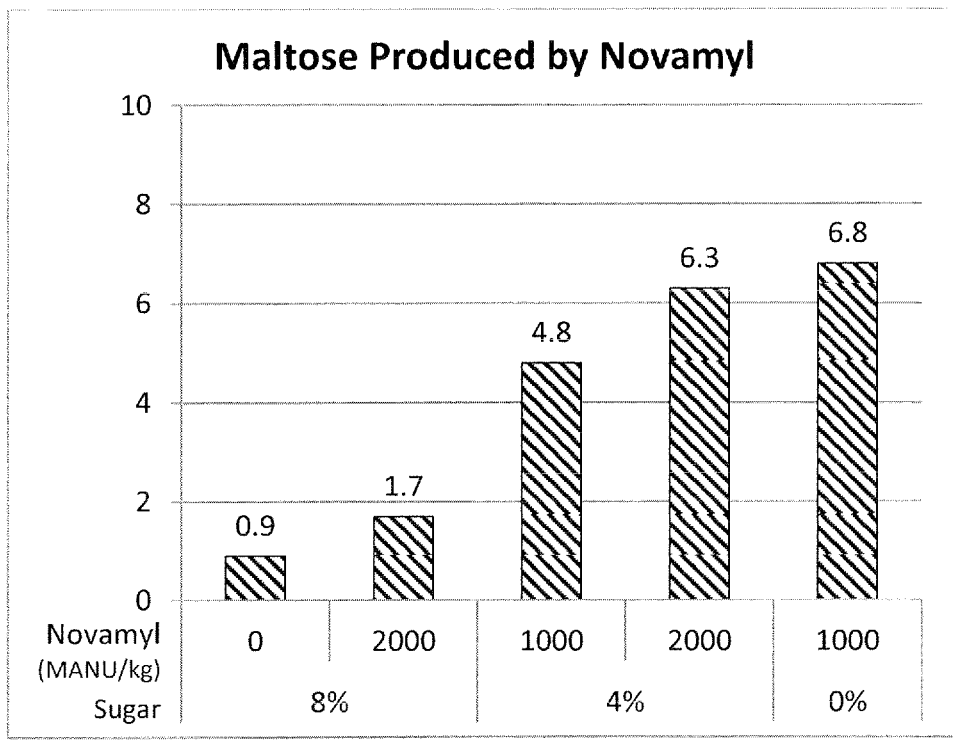
FIG. 8 is a graph showing the effects of reducing the added sugar, or sucrose, in dough formulas on the performance of anti-staling enzymes in terms of the amount of the enzyme end-product (i.e., maltose) produced in the bread from Example 3.

FIG. 8 shows the amounts of maltose produced by the anti-staling enzyme, NOVAMYL® in this baking test. Maltose is an end product of NOVAMYL® action, and the amount of maltose produced in the bread is directly related to the functionality of the enzyme. The test results in FIG. 8 show that by reducing or removing the added-sugar (i.e., the enzyme inhibitor) in the dough, more maltose was produced by NOVAMYL®, which corresponds with an increase in enzymatic activity and functionality. The increased activity of NOVAMYL® not only improved the anti-staling effect of the enzyme, but also resulted in high maltose levels in the bread, which made positive contributions to the taste and flavor of the finished bread.

In this example, the inventive enzyme composition and without any added sugar the level of yeast addition could be reduced from 3.0% to 2.0%, representing a 33% of yeast reduction.

Example 4

Combination of AMGs

This example examines the combination of a regular RSD amyloglucosidase, AMG 1100, and a thermally-stable amyloglucosidase, Po-AMG, in a 0% added-sugar baking. A white bread dough was prepared using a no-time system. In this baking, 2000 MANU/kg flour of NOVAMYL® 3D, which is a variant of NOVAMYL®, was used as the anti-staling enzyme. AMG 1100 was used as the RSD amyloglucosidase, along with the thermally-stable amyloglucosidase Po-AMG. The level of RSD amyloglucosidase, AMG 1100, was at 500 and 1000 AGU/kg flour, whereas the level of the thermally-stable amyloglucosidase, Po-AMG, was tested at 545 AGU/kg and 1089 AGU/kg flour.

White Pan Bread—No-Time

| Ingredients | % of flour weight | Gram |
|---|---|---|
| Flour | 100.0 | 700 |
| DEPENDOX ® AXC | 0.06 | 0.42 |
| Salt | 2.0 | 14 |
| Granulated sugar (sucrose) | Vary | Vary |
| Calcium Propionate | 0.3 | 2.1 |
| SSL (optional) | 0.35 | 2.45 |
| GMS-90 | 1.00 | 7 |
| Soy Oil | 2.0 | 14 |
| Compressed Yeast | Vary | Vary |
| Water | Vary | Vary |
| Total Weight | Vary | Vary |

Formula Variations

| Dough # | 1 | 2 | 3 | 4 |
|---|---|---|---|---|
| Added Sugar (sucrose- % of flour weight) | 8 | 8 | 0 | 0 |
| UFP 250 (% of flour weight) | 0 | 0.25 | 0 | 0 |
| NOVAMYL ® 3D (% of flour weight) | 0 | 0 | 0.02 | 0.02 |
| Eversoft[4] (% of flour weight) | 0 | 0 | 0.0025 | 0.0025 |
| AMG 1100 (AGU/kg flour) | 0 | 0 | 545 | 1089 |
| Po-AMG (AGU/kg flour) | 0 | 0 | 1000 | 500 |
| Compressed Yeast (% of flour weight) | 5.75 | 5.75 | 4.0 | 4.0 |
| Water (% of flour weight) | 60.0 | 60.0 | 64.0 | 64.0 |

[4] A bacterial amylase product from Corbion

Figure 9:
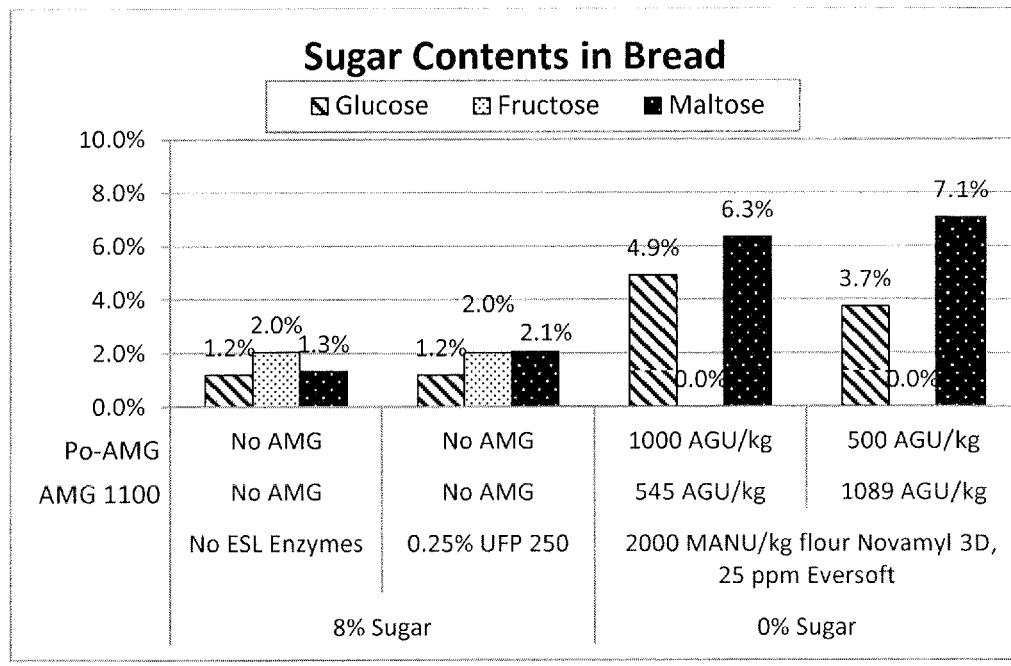
FIG. 9 is a graph comparing the glucose, fructose, and maltose contents in various bread formulations in Example 4.
Figure 10:
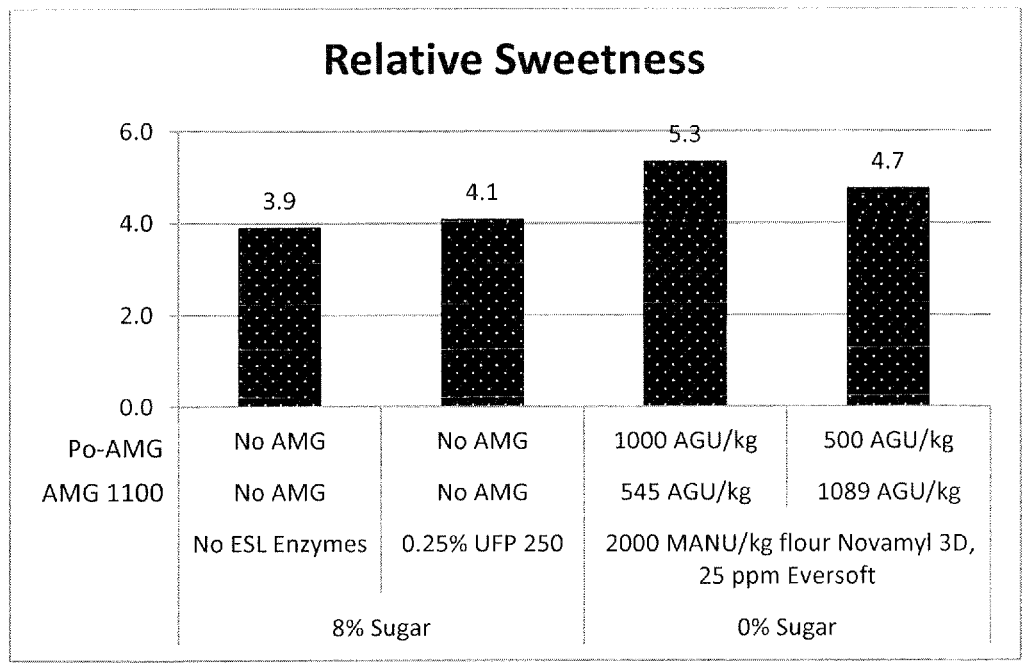
FIG. 10 is a graph of the relative sweetness of the different bread formulations in Example 4.
Figure 12:
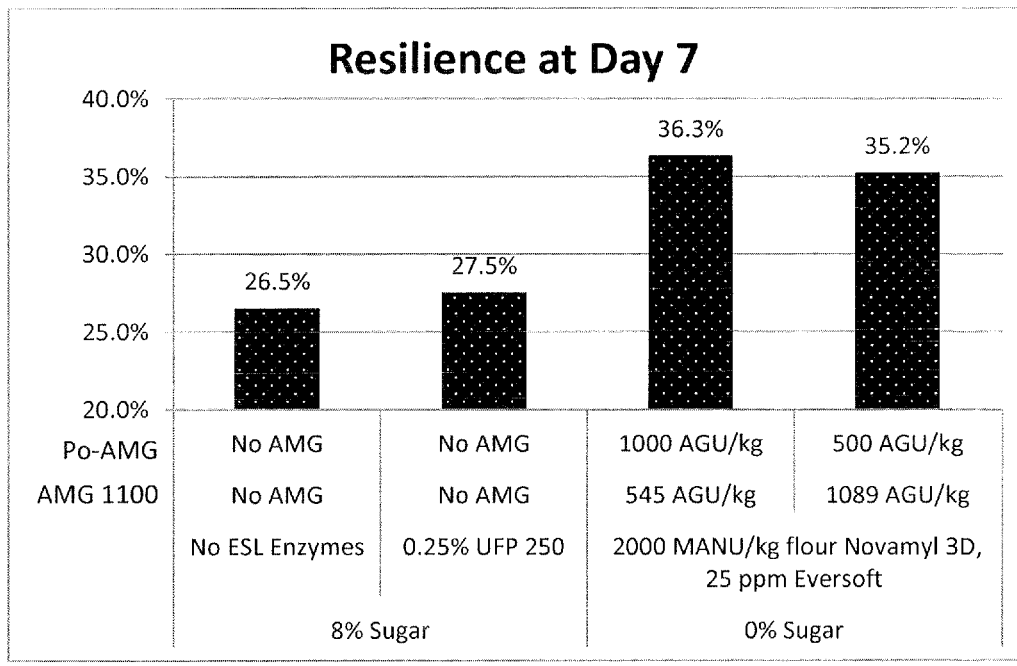
FIG. 12 is a graph of the resilience of the different bread formulations in Example 4.
Figure 13:
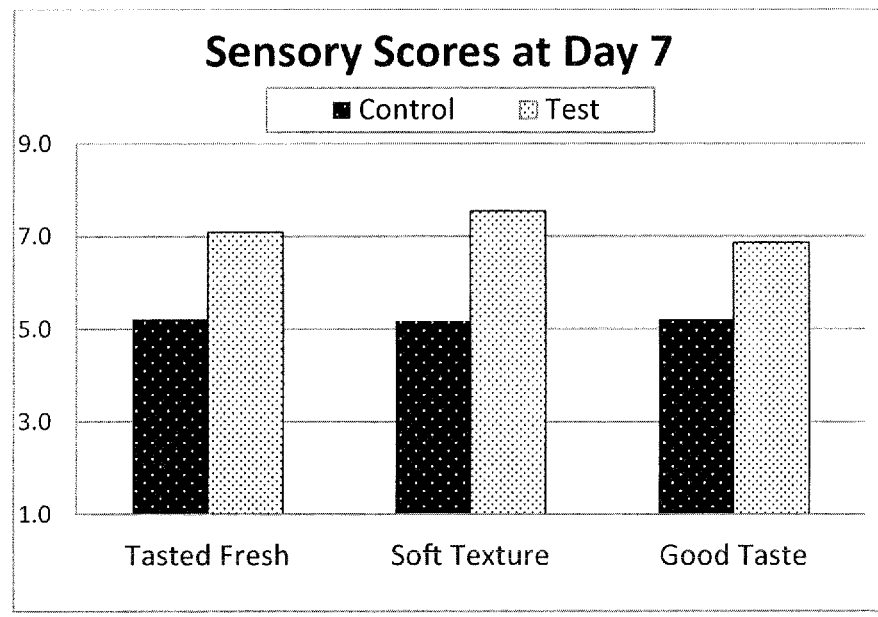
FIG. 13 shows sensory results comparing a control bread to the test bread formulated in Example 5.
Figure 14:
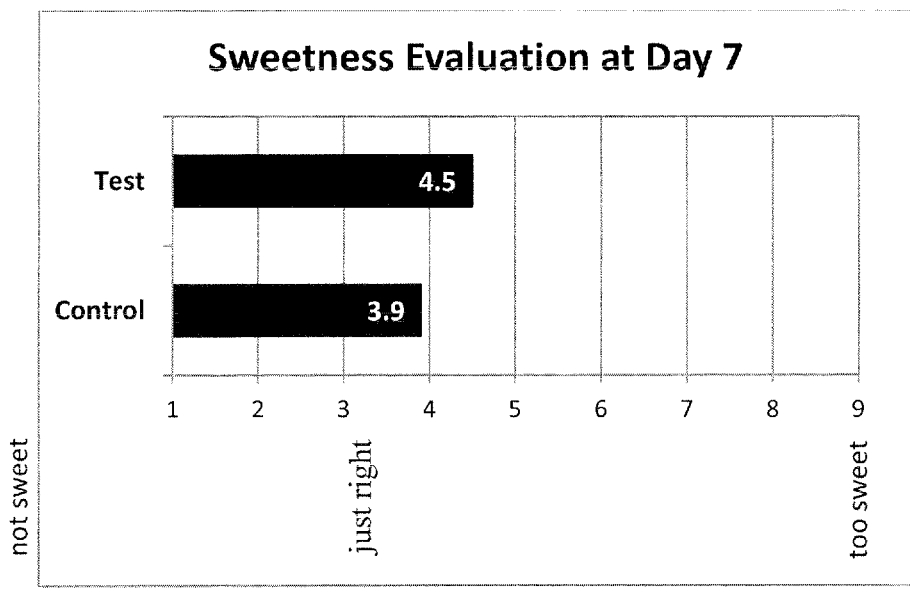
FIG. 14 provides sensory evaluation results showing the sweetness of a control bread compared to the test bread formulated in Example 5.

After baking, bread loaves were store in plastic bags for shelf life study. For sugar analysis, bread crumbs were extracted with distilled water, and the sugar content was analyzed on the Dionex HPLC system. FIG. 9 shows the sugar types and content in the bread. The results showed that with the addition of the anti-staling enzyme and both types of amyloglucosidases, AMG 1100 and Po-AMG, significant amounts of glucose and maltose were produced in the bread. However, there was no detectable amount of fructose in that bread made with 0% added sugar and the invention enzyme compositions. FIG. 10 showed the calculated sweetness based on the measured sugar contents for those bread samples. The results showed that with the addition of enzymes (both NOVAMYL® 3D and the two AMGs), the bread with 0% of added-sugar were actually sweeter than the control bread made with 8% added-sugar. FIGS. 11-12 showed that with the addition of the enzymes, bread staling was significantly slowed, which can be measured by the decrease of crumb firmness and increase of crumb resilience. Again, in this example, the dough made with the inventive enzyme formulation and 0% added sugar allowed a 30% yeast reduction, when compared to the dough with 8% added sugar and without the inventive enzyme formulation.

Some of the improvements with respect to crumb resilience and adhesiveness (calculated from FIGS. 2, 3, 11, and 12) are summarized in the following table:

| | | AMG (AGU/kg flour) | | | | | |
|---|---|---|---|---|---|---|---|
| | | 0 | 500 | 1,000 | 2,000 | 5,000 | FIG. 7 |
| Resilience | AMG 1100 | 28.2% | 28.4% | 28.8% | 31.2% | 32.3% | 27.50% |
| | Po-AMG | 28.2% | 31.3% | 33.3% | 38.2% | 41.5% | 35.20% |
| Resilience Improvement | | | 10% | 16% | 22% | 28% | 28% |
| Adhesiveness | AMG 1100 | 12.4 | 12 | 11.9 | 10.4 | 8.5 | |
| | Po-AMG | 12.4 | 10.6 | 6.4 | 3.7 | 1.8 | |
| Adhesiveness Improvement | | | 12% | 46% | 64% | 79% | |

Example 5

Sensory Validation

In this Example, breads were prepared and evaluated for sensory perception. A control bread made with 8% of added-sugar (sucrose) and 6.65 Promu/kg Novamyl Pro, which is a variant of NOVAMYL® (available from Novozymes), was compared to a test bread made with 0% of added-sugar, 33.25 PROMU/kg Novamyl Pro, and a combination of a raw starch degrading AMG (Gold Crust 3300 from Novozymes) and Po-AMG.

Sponge and Dough System

| | % of flour weight | 900 g dough |
|---|---|---|
| Sponge | | |
| Polar Bear Flour | 70 | 630.0 |
| STARPLEX ® | 0.25 | 2.3 |
| SSL | 0.375 | 3.4 |
| Compressed Yeast | 3 | 27.0 |
| Water | 40.5 | 364.5 |
| Total | 114.13 | 1027.1 |
| Dough | | |
| Polar Bear Flour | 30.00 | 270.0 |
| Sugar (sucrose) | Vary | Vary |
| Salt | 2 | 18.0 |
| Calcium Propionate | 0.35 | 3.2 |
| DEPENDOX ® AXC | 0.06 | 0.54 |
| Soybean Oil | 2 | 18.0 |
| Compressed Yeast | Vary | Vary |
| Water | Vary | Vary |

Formula Variations in Dough Side

| Dough # | 1 | 2 |
|---|---|---|
| Added Sugar (sucrose- % of flour weight) | 8 | 0 |
| NOVAMYL ®Pro [A] PROMU/kg flour | 6.65 | 33.25 |
| Gold Crust 3300 [B] (AGU/kg flour) | 0 | 825 |
| Po-AMG (AGU/kg flour) | 0 | 756 |
| Yeast Compressed (% of flour weight) | 4.0 | 2.5 |
| Water (% of flour weight) | 14.0 | 18.0 |

Figure 15:
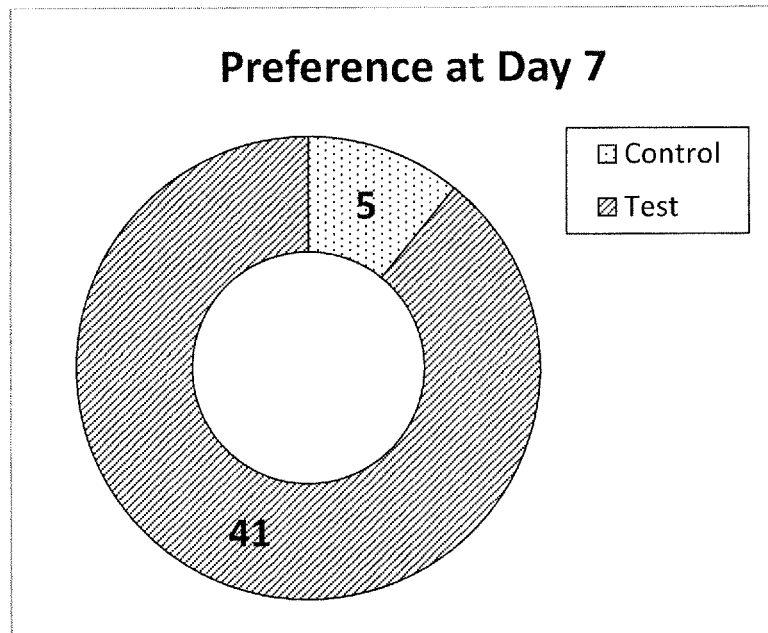
FIG. 15 shows sensory preference results of a control bread compared to the test bread formulated in Example 5.
Figure 16:
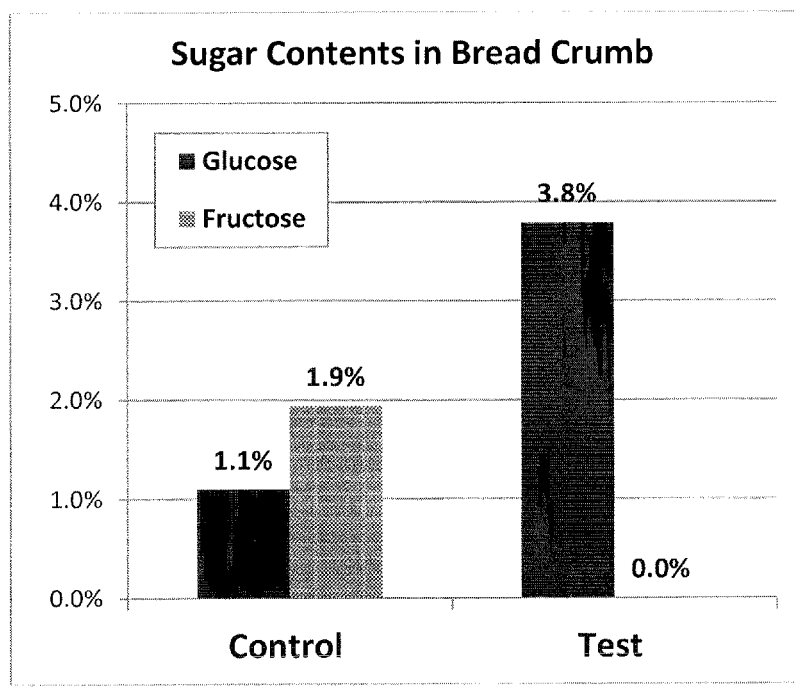
FIG. 16 is a graph showing the sugar contents of a control bread compared to a test bread according to the invention in Example 5.

[A] A NOVAMYL variant from Novozymes
[B] A Talaromyces emersoni amyloglucosidase from Novozymes FIG. 13-16 showed a sensory comparison, with 46 panelists, of a control bread made with 8% of granulated sugar (sucrose) and 6.65 PROMU/kg of NOVAMYL® Pro, to a test bread made with 0% added-sugar, 33.25 PROMU/kg of NOVAMYL® Pro, 825 AGU/kg of Gold Crust 3300, and 756 AGU/kg of Po-AMG. The results showed that the test bread with 0% added-sugar was scored significantly higher in freshness, soft texture, and good taste. A sweetness evaluation also showed the test bread was tasted slightly sweeter than the control bread and it is more close to "just right" sweetness. Overall, about 90% of panelists (41 out of 46) preferred the test bread made with zero percent of added-sugar (FIG. 15). The sugar contents analysis (FIG.

16) again showed that the test bread made with no added sugar but with the inventive enzyme composition was fructose-free.

We claim:

1. A method of forming a bakery product, said method comprising:
providing a dough comprising:
yeast;
a source of starch;
about 500 AGU/kg flour to about 1,000 AGU/kg flour of a thermally-stable amyloglucosidase that exhibits activity during baking at temperatures at which the starch gelatinizes; and
about 500 AGU/kg flour to about 1000 AGU/kg flour of a raw starch degrading amyloglucosidase, wherein ratio of enzymatic activity of the thermally-stable amyloglucosidase and the raw starch degrading amyloglucosidase is about 1:2 to about 2:1, wherein said thermally-stable amyloglucosidase and said raw starch degrading amyloglucosidase have respective optimum temperatures, with the optimum temperature of said raw starch degrading amyloglucosidase being lower than the optimum temperature of said thermally-stable amyloglucosidase;
about 2000 MANU/kg flour of an anti-staling enzyme; and
baking the dough for a time and temperature sufficient to yield the bakery product,
wherein the bakery product has a total sugar level in the range of from about 6 to about 12% by weight, and wherein the total sugar level includes glucose, fructose, and maltose; and
wherein the bakery product has the glucose level of at least about 3% by weight and
the fructose level of less than about 0.5% by weight.

2. The method of claim 1, wherein said dough, prior to proofing, comprises less than about 1% by weight sugar, based upon the total weight of the dough taken as 100% by weight.

3. The method of claim 1, said thermally-stable amyloglucosidase having an optimum temperature of about 60° C. or greater.

4. The method of claim 1, said raw starch degrading amyloglucosidase having an optimum temperature of about 65° C. or lower.

5. The method of claim 1, said thermally-stable amyloglucosidase having an optimum temperature of about 60° C. to about 85° C., and said raw starch degrading amyloglucosidase having an optimum temperature of about 40° C. to about 55° C.

6. The method of claim 1, wherein said thermally-stable amyloglucosidase is derived from strains selected from the group consisting of *Penicillium oxalicum, Talaromyces emersonii, Talaromyces duponti, Talaromyces thermophilius, Clostridium thermoamylolyticum*, and *Clostridium thermohydrosulfuricum*.

7. The method of claim 6, wherein said thermally-stable amyloglucosidase is derived from *Penicillium oxalicum*.

8. The method of claim 1, said dough having an initial quantity of sugar and further comprising proofing said dough prior to said baking so as to form a proofed dough, wherein during said proofing, the thermally-stable amyloglucosidase and the raw starch degrading amyloglucosidase convert at least some starch into glucose.

9. The method of claim 8, wherein:
said initial quantity of sugar is about 0% by weight, based on the weight of the dough taken as 100% by weight; and
said proofed dough comprises about 1% by weight or greater sugar, based on the weight of the proofed dough taken as 100% by weight.

10. The method of claim 9, wherein during baking said starch gelatinizes and said thermally-stable amyloglucosidase hydrolyzes the gelatinized starch to produce glucose.

11. The method of claim 1, wherein said dough, prior to proofing, comprises about 0% by weight added sugar, based upon the total weight of the dough taken as 100% by weight.

12. A method of forming a bakery product, said method comprising:
providing a dough comprising:
yeast;
an initial quantity of sugar;
a source of starch;
about 500 to about 1,000 AGU/kg flour of a thermally-stable amyloglucosidase that exhibits activity at temperatures at which the starch gelatinizes;
about 500 to about 1000 AGU/kg flour of a raw starch degrading amyloglucosidase, wherein ratio of enzymatic activity of the thermally-stable amyloglucosidase and the raw starch degrading amyloglucosidase is about 1:2 to about 2:1; and
about 2000 MANU/kg flour of an anti-staling amylase; and
baking the dough for a time and temperature sufficient to yield the bakery product, said bakery product having a final quantity of sugar that is greater than said initial quantity of sugar and one or more of:
a percent resilience of at least about 28% when measured at shelf life day 7;
a firmness of less than about 250 g of force at shelf life day 7; or
an adhesiveness of about 5 g*mm to about 25 g*mm when measured at shelf life day 7.

13. The method of claim 12, wherein said bakery product having two of said percent resilience, said firmness, or said adhesiveness.

14. The method of claim 12, wherein said bakery product having each of said percent resilience, said firmness, and said adhesiveness.

15. The method of claim 12, wherein said thermally-stable amyloglucosidase is derived from strains selected from the group consisting of *Penicillium oxalicum, Talaromyces emersonii, Talaromyces duponti, Talaromyces thermophilius, Clostridium thermoamylolyticum*, and *Clostridium thermohydrosulfuricum*.

16. The method of claim 12, wherein said initial quantity of sugar is less than about 3% by weight, based on the weight of the dough taken as 100% by weight.

* * * * *